US008717843B2

(12) United States Patent
Cerofolini

(10) Patent No.: US 8,717,843 B2
(45) Date of Patent: May 6, 2014

(54) METHOD AND APPARATUS FOR ULTRASOUND IMAGE ACQUISITION

(71) Applicant: ESAOTE S.P.A., Milan (IT)

(72) Inventor: Marino Cerofolini, Subbiano (IT)

(73) Assignee: Esaota S.p.A., Genoa (IT)

(*) Notice: Subject to any disclaimer, the term of this patent is extended or adjusted under 35 U.S.C. 154(b) by 0 days.

(21) Appl. No.: 13/670,118

(22) Filed: Nov. 6, 2012

(65) Prior Publication Data

US 2013/0064037 A1 Mar. 14, 2013

Related U.S. Application Data

(63) Continuation of application No. PCT/IB2011/052000, filed on May 5, 2011.

(30) Foreign Application Priority Data

May 7, 2010 (IT) ................................. GE2010A047
May 7, 2010 (IT) ................................. GE2010A048

(51) Int. Cl.
*G01H 3/00* (2006.01)
*G01H 3/12* (2006.01)

(52) U.S. Cl.
CPC ..................................... *G01H 3/125* (2013.01)
USPC ............................................................ 367/7

(58) Field of Classification Search
USPC ................................................................ 367/7
See application file for complete search history.

(56) References Cited

U.S. PATENT DOCUMENTS

| | | | | |
|---|---|---|---|---|
| 6,251,073 | B1* | 6/2001 | Imran et al. | 600/443 |
| 6,416,475 | B1* | 7/2002 | Hwang et al. | 600/441 |
| 6,780,154 | B2* | 8/2004 | Hunt et al. | 600/446 |
| 7,611,463 | B2* | 11/2009 | Shah | 600/437 |
| 7,809,400 | B1* | 10/2010 | Hwang | 455/550.1 |
| 7,891,230 | B2* | 2/2011 | Randall | 73/1.82 |
| 8,312,771 | B2* | 11/2012 | Randall et al. | 73/627 |
| 8,320,429 | B2* | 11/2012 | Kang et al. | 375/148 |
| 2002/0016545 | A1 | 2/2002 | Quistgaard | |
| 2003/0139664 | A1 | 7/2003 | Hunt | |
| 2008/0114253 | A1 | 5/2008 | Randall | |
| 2009/0105592 | A1* | 4/2009 | Yao | 600/447 |

FOREIGN PATENT DOCUMENTS

EP 2053418 4/2009

OTHER PUBLICATIONS

Written Opinion of the International Search Authority. For Application PCT/IB2011/052000. (Nov. 13, 2012).*

(Continued)

*Primary Examiner* — Isam Alsomiri
*Assistant Examiner* — James Hulka
(74) *Attorney, Agent, or Firm* — Themis Law

(57) ABSTRACT

Apparatus for ultrasound image acquisition is integrated into the casing of an ultrasound probe that includes an array of electro-acoustic transducers, which transmit and receive ultrasound pulses. The array communicate with a processing unit, to which reception signals are fed, and are connected to a unit generating signals for exciting the transmission of ultrasound waves. In one aspect of the invention, at least the processing unit is fitted into the probe casing and is configured to convert the reception signals into an image, and to generate video signals for generating an image on a display unit. The transmission between the probe and a remote unit displaying and possibly storing the images as video signals may be operated wirelessly.

19 Claims, 17 Drawing Sheets

(56) References Cited

OTHER PUBLICATIONS

Ellis M A et al, Reduced rank formulation for increased computational efficiency in medical ultrasound model-based beamforming, Signals, Systems and Computers, 2008 42nd Asilomar Conference, IEEE, Piscataway, NY, US, Oct. 26, 2008, pp. 1923-1926.

Francesco Viola et al, Time-Domain Optimized Near-Field Estimator for Ultrasound Imaging: Initial Developments and Results, IEEE Transactions on Medical Imaging, IEEE Service Center, Piscataway, NJ, US, vol. 27, No. 1, Jan. 1, 2008, pp. 99-110.

* cited by examiner

METHOD AND APPARATUS FOR ULTRASOUND IMAGE ACQUISITION

CROSS-REFERENCE TO RELATED APPLICATIONS

The present application is a continuation of international application PCT/IB2001/052000 having an international filing date of May 5, 2001, which claims priority to Italian patent applications GE2010A000047 and GE2010A000047 each having a filing date of May 7, 2010, all of which are incorporated herein by reference in their entireties.

FIELD OF THE INVENTION

The present invention relates to an apparatus for ultrasound image acquisition integrated into the casing of an ultrasound probe for ultrasound imaging apparatuses, wherein the probe comprises, an array of electro-acoustic transducers, each of which transmits ultrasound waves when powered with an electric excitation signal and generates an electric reception signal when impinged by an ultrasound wave or pulse generated, for example, by the reflection of ultrasound waves transmitted therefrom;

the array of electro-acoustic transducers being provided with at least a communication line to a processing unit, through which each transducer of the array of transducers feeds reception signals to a processing unit, and with a communication line, through which the electric excitation signals generated by a generating unit are fed to each transducer of the array of transducers for exciting the transducer to transmit ultrasound waves;

the generating unit comprising excitation signal generating means and means for feeding the signals to the array of transducers.

BACKGROUND OF THE INVENTION

The structure described above is a typical structure of a so-called ultrasound probe, particularly of an ultrasound probe used for ultrasound diagnostic imaging. Generally, ultrasound transducers are piezoelectric elements, typically elements made of a ceramic material, where oscillations of the crystal lattice are generated upon excitation with an electric potential and generate mechanical waves in the frequency range of ultrasound acoustic waves. The frequency of the waves and the shape and the spectral composition of the generated ultrasound waves depend on the frequency, shape and spectral composition of the electric excitation pulse.

Typical ultrasound probes of the prior art are therefore composed of a structure as described hereinbefore and are connected to a remote display unit, which allows signals transmitted from the probe to be displayed, stored and processed and at the same time powers the probe.

The invention provides a highly portable probe that does not have cable connections to a remote display unit. Several attempts have been made to produce a probe of this type, and generally two types are the most investigated.

With reference to a first type, the idea of making ultrasound diagnoses with a wireless probe has been handled by providing a real portable ultrasound apparatus having a compact size with respect to conventional apparatus, such that the user can easily use the apparatus with one hand.

With reference to another type, an attempt was made to integrate the beamformer into the probe and transmit the obtained data to a remote display unit, such as an ultrasound apparatus, by radio frequency signals.

However, in both the above cases the apparatuses have considerable dimensions, have usage problems and moreover the quality of the reconstructed image is considerably poorer than that generated by conventional ultrasound apparatus.

Therefore, there is the unsatisfied need of producing an ultrasound probe for ultrasound imaging apparatus, particularly for diagnostic purposes that, by relatively simple and inexpensive arrangements, allows the probe and a remote display unit to communicate in a wireless mode, in order to facilitate the ultrasound imaging examination procedure without creating obstacles or limitations for the presence of communication cables between the probe and the remote units.

SUMMARY OF THE INVENTION

The invention achieves the above aims by providing an ultrasound probe of the type described above wherein at least the processing unit is mounted within the probe casing and comprises means for converting the reception signals into an image, as well as video signal generating means for generating an image on a display unit, wireless communication means being provided for the transmission between the probe and a remote unit displaying, which stores said images as video signals.

By the provision of converting means into the processing unit, which receives the reception signals and converts them into image data that are transmitted to video signal generating means converting such data into a video signal, the processed data occupy a frequency band for the transmission that is much lower than that of conventional ultrasound images and therefore the processed data can be easily transmitted in wireless mode.

With reference to all the known solutions used up to now, the received data are processed outside the probe and therefore the transmission from the probe to a remote display unit, by means of wireless protocols, involves raw received data. In this case, the necessary bandwidth for transmitting such data is very high, therefore, such systems do not find a real practical use as the transmission is too slow. This, for example, occurs in the apparatus described in US2002/0016545. In this document, the image data are obtained by using conventional ultrasound image forming technologies, therefore the miniaturization has a limit of a few kilos (about 5 pounds). In order to reduce weight and the dimensions by using known ultrasound technologies, the apparatus converts the reception signals into raw signals, which are transmitted to the remote unit to be further processed as an image and to be displayed.

According to a preferred improvement of the invention that allows dimensions and weights of the processing unit to be reduced to the typical size of ultrasound probes and therefore to less than 500 grams, the processing means comprise a storage unit wherein sequences of time windows for exciting the individual transducers to transmit ultrasound pulses are stored. Such windows are defined to cause an acoustic transmission pulse to be successively transmitted in the form of a spherical wave from each of a plurality of transmitting points arranged all along the array of transmitting transducers, wherein sequences of time windows for the reception of reflection pulses of the transmitted pulses are stored. The reflection pulses are converted into reception signals by each transducer during the corresponding reception time window of the transducer, the reception window being calculated beforehand for each point of a set of predetermined reflection points ($P_{1,1} \ldots P_{n,n}$) arranged at a predetermined distance one from the other to form a grid of predetermined reflection points extending in the scan plane or slice along which the body under examination is imaged. Therefore, the successive transmission of an acoustic transmission pulse in the form of a spherical wave from each of a plurality of transmitting points is arranged all along the array of transmitting transducers and the set of reflection signals is defined from the individual reflection points ($P_{1,1}$ ... $P_{n,n}$) of said grid of predetermined reflection points for each spherical transmission pulse transmitted by a different transmission point.

Otherwise, said converting means calculate, in real time and every time, said time windows.

The converting means comprise an image forming storage, wherein the sets of reflection signals for each of the spherical transmission pulses transmitted by the individual transmitting points are stored with the storage means, and the image along the scan plane or slice of the body under examination is generated by summing the reflection signals of the sets of reflection signals generated by the individual spherical transmission pulses transmitted by the various transmitting points.

According to another aspect of the invention, the image forming storage comprises one or more storage cells where image data are stored for each set of reflection signals from the individual reflection points of the grid of predetermined reflection points, so that the processing means generate a single final image by summing the image data concerning each set of reflection signals contained in the corresponding storage cells, each storage cell being univocally associated to an image pixel.

By means of a configuration such as the above described configuration, it is advantageous for each storage cell to be univocally associated to a reflection point of the grid of the reflection points and the components of the reception signals corresponding to the reflection signals related to the reflection point are stored therein. Those components are determined by the time reception windows, each being calculated for the reception of the reflection signal from a predetermined reflection point of the grid of the reflection points.

The above described improvements operate according to an image forming method that includes the steps of transmitting ultrasound pulses into a body under examination, receiving reflection pulses from the body under examination, transforming the reflection pulses into reception signals, converting the reception signals into an image and displaying the image. The transmission pulses are transmitted from a plurality of electro-acoustic transmitting transducers and the reception pulses from a plurality of electro-acoustic reflection transducers, which are actuated respectively for transmission and reception according to predetermined rules focusing the transmitted or received acoustic beam on individual points and/or on two-dimensional or three-dimensional regions of the body under examination. Unlike conventional ultrasound techniques, a predetermined fixed grid of reflection points in the scan plane or volume defined by the array of transmitting and receiving transducers is defined, the time windows actuating the transducers for the reception and/or transmission being defined only for the transmission/reception of the signal contributions deriving from each of said reflection points of the predetermined transmission grid. The signal contributions deriving from at least each reflection point of the grid of reflection points are stored separately for each different point, while the contributions of the reflection signal of each reflection point are summed together and constitute a signal corresponding to the pixel or voxel of the ultrasound image in the position corresponding to the image of the body under examination in the reflection point, while the set of pixels and voxels obtained thereby is encoded as a video signal and is transmitted by wireless mode to a remote reproducing/display unit.

In one embodiment, the method provides for the transmission of ultrasound pulses towards a body under examination;

the pulses are generated by transmitting transducers which are grouped into an array of transmitting transducers;

the transmitting transducers are each connected to an electric excitation pulse generator and transform the electric pulses into acoustic pulses;

the reception of the reflection acoustic pulses generated upon reflection of the transmission pulses by the structural elements of the body under examination have acoustic reflector features captured by receiving transducers;

the receiving transducers are grouped into an array;

the receiving transducers are each connected to processing means;

each receiving transducer provides to the processing means an electric reception signal generated by the excitation of the transducer upon reception of the reflection acoustic signal impinging upon the receiving transducer;

the reception signals provided by the individual receiving transducers is combined by the reception signal processing means and the combination occurs with relative time shifts of the reception signals of the individual receiving transducers, the shifts being such that the individual components of the reception signals of the individual receiving transducers are combined together and correspond to the components of the reflection signal generated by the reflection of the transmission pulse by a predetermined reflector of the structure of the body under examination which has a predetermined position with respect to the array of receiving transducers;

the step combining the reception signals of the individual receiving transducers is repeated with different time shifts, to obtain a combination of the components of the reception signals caused by the reflection of the transmission signal by each of the reflectors of the structure of the body under examination in a predetermined scan plane or a predetermined slice of the body under examination, the scan plane or which slice being parallel to the direction of propagation of the transmission pulse and the reflection signals;

a set of predetermined reflection points is defined, which is arranged at a predetermined distance from each other and forms a grid of predetermined reflection points extending in the scan plane or slice along which the body under examination is imaged;

the time shift of the reception signals for determining the transmission pulse reflection signal from each of the predetermined reflection points is defined beforehand according to predetermined relative distances between the individual reflection points, the determination of the reflection signal occurring by combining the components of the reception signals of the individual receiving transducers, the components falling within time intervals of the reception signals that have the delays and deriving from the corresponding components of the reflection signal determined by each of the predetermined reflection points;

an acoustic transmission pulse is successively transmitted in the form of a spherical wave from each of a plurality of transmitting points all along the array of transmitting transducers;

the set of reflection signals is determined from the individual reflection points of the grid of predetermined reflection points for each spherical transmission pulse transmitted by a different transmitting point and separately stored for each of the spherical transmission pulses transmitted by the individual transmitting points; and an image is generated along the scan plane or slice of the body under examination by summing the reflection signals of the sets of reflection signals generated by the individual spherical transmission pulses transmitted by the various transmitting points.

According to a further improvement of the apparatus of the present invention, there are provided means for determining a sub-grid, smaller than said grid, whose peripheral points coincide with at least part of the points of said grid, said sub-grid being composed of as many points as those contained in said grid in the area delimited by the peripheral points of said sub-grid or more.

In another embodiment, the sub-grid is composed of as many points as those contained in the grid, since it is optimized for the computing power of the processing means.

In another embodiment, there is provided a user interface for displaying the obtained image or video and for setting the perimeter of the sub-grid, a computational algorithm being provided for automatically defining the internal points of the sub-grid.

Therefore, a user can make a first scanning and obtain an image or a series of images or videos, can decide the region of interest where to make a more detailed imaging, and with the user interface that can launch the computational algorithm that automatically defines the internal points of the sub-grid.

Thus the following acquisitions are limited to the region of interest, with a more detailed level than the first acquisition due to the smaller dimensions of the region of interest and because the same number of reflection points under examination is maintained contemporaneously.

An apparatus according to the invention can have additional functional and constructional features to achieve an ultrasound system having a probe with a substantially conventional shape and weight, wherein the electronic components scanning and forming the image from the conversion of received data into finished image data are integrated and wherein the probe communicates wirelessly with a remote unit displaying/storing the images.

Any type of protocol of the transmission and reception protocol may be used. In a preferred embodiment the transmission and reception is with a wi-fi radio wave type.

Preferably each transducer of the array of transducers is connected to the processing unit and to the generating unit by a switch, which has two conditions, an operating condition, enabling each transducer to receive/transmit electric excitation signals, and a non-operating condition, disabling each transducer from receiving/transmitting electric excitation signals, respectively. The transition from the operating condition to the non-operating condition is set by the processing unit that alternates the reception/transmission of each individual transducer according to specific time sequences that are different for each individual transducer.

In this case the processing unit can include storage devices and one or more programmable components configured to control the operating process, to synthesize waveforms for exciting the transducers and to combine the components of the reception signals according to appropriate rules in order to obtain image data directly. The processing unit therefore can manage both the storage of reception signals of the individual transducers in suitable storage devices and the reading of the stored reception signals.

In one embodiment, an ultrasound probe according to the invention provides for powering electronic circuits with a power generating and storing source, such as a battery or the like, disposed in combination with and connected to circuits matching and connecting the battery to the electric signal generating, communicating and processing means. This feature is particularly advantageous, since it allows a probe according to the invention to be made independent from any type of power supply obtained by a physical connection to any external network, enhancing the independence of the probe from any other apparatus, whether power supply apparatus, due to the use of the battery, or remote display equipment, due to the use of wireless communication.

It has to be noted that such power supply is provided within the probe. It will be described below in detail how the battery is housed within the casing of the probe.

It is also possible to provide within the probe the unit generating the transmission signals to be sent to excite the transducers. Such signals are preferably time-varying frequency signals, the transmitted ultrasound pulses being encoded by frequency variations over time according to a specific function over time, such as, for example, a linear or non-linear function. In particular, "CHIRP" signals are generated whose frequency variation over time provides for high quality images even when the number of transmission and reception channels between the transducer array is drastically reduced and the signal generating and processing units reduces the overall dimensions of the probe, thus facilitating the use thereof.

The choice of arranging the means communicating, feeding, processing and generating the received and/or transmitted signals into the probe inevitably leads to problems in the size of the probe, therefore an ultrasound probe according to the invention in a preferred embodiment has a particular and characteristic structure which allows all of the above described means described above to be housed therein while being as easy to use as conventional probes. The handling of the probe is also improved by removing obstacles, if any, when moving it. Such obstacles may be due to the presence of cables for the connection to external units.

The probe casing that houses all of the above described elements is composed of a case comprising two narrower and longer side faces and two wider and longer faces, parallel to each other and oriented lengthwise in the direction of a longitudinal axis along the direction of propagation of the acoustic beam transmitted from the probe. Moreover, there are provided two boards that are parallel or substantially parallel to the wider faces. The circuits feeding, generating and processing the transmitted and/or received signals are arranged on those boards.

Such boards are supported by supporting means, allowing the boards to be arranged parallel to each other and allowing also a region housing the power storing and/or generating means to be formed. For example, it is possible to provide an intermediate supporting frame that keeps the boards spaced apart and that allows the battery to be housed in the space between the two boards. Preferably, the frame is composed of a peripheral rim having a thickness substantially corresponding to the thickness of the battery and/or to the gap between the two boards. Such rim delimits a central space between the two boards for housing the battery. In this case, there is provided a plate closing at least one of the open sides of the frame, allowing the frame to rest on such plate to form the bottom of the housing space that comprises the contacts for the connection between the battery and the boards, such to power the means generating and processing the transmitted and/or received signals that are provided on the boards.

Preferably, the means feeding, generating and processing the transmitted and/or received signals are made as printed electric circuits on the two boards and are fastened to the frame, and are oriented parallel to the larger faces of the probe casing.

In one embodiment, both the processing unit and the generating unit comprise processor means executing a logic program processing, transmitting and receiving signals and a storage unit intended to store the program, the data for executing the program and the data resulting from the execution.

Preferably the processing unit is composed of a FPGA device (Field Programmable Gate Array) that receives the signals of the transducers by an analog/digital converter that transforms the input signals of the FPGA device into digital data, such that they can be processed by the device.

Moreover, such device has the great advantage of being programmable and the user can modify the program, by changing the task of the probe depending on the needs required by the type of examination to be performed.

Therefore it is necessary to provide a user interface allowing the FPGA to be programmed for manually controlling the scanning parameters. In this case the wireless communication means receive from such interface control signals and/or codes for programming and setting the operational conditions of the processing and generating units.

Such interface can be directly mounted on the probe, or, as it will be described below, can belong to a remote display unit that sends, in a wireless mode, the control signals to the communication means.

The transducer array and the wireless communication means are fastened at the ends of the boards respectively. There are provided contacts for the communication with the transducer array and with the wireless communication means, which are composed of a plug connector a first part of which cooperating with a corresponding second part.

The contacts of the first part of the plug connector are fastened to the inputs and/or outputs of the array of transducers and to inputs and/or outputs of the wireless communication means respectively and the contacts of the second part are at the ends of the two boards, such that both the transducer array and the wireless communication means are connected to the means feeding, generating and processing the transmitted and/or received signals.

A variant embodiment of the present invention provides the transducer array and/or the wireless communication means to be removably mounted to the probe casing, such that it is possible to use different transducer arrays and/or different communication means while maintaining the same control electronics of the probe. In this case the communication contacts are composed of electric/mechanical connection elements composed in turn of a first part of a plug connector cooperating with a corresponding second part of a plug connector, with the first part fastened to the inputs/outputs of the transducer array and to the input/outputs of the wireless communication means respectively and the second part being fastened to the ends of the two boards and/or to the corresponding shorter and narrower sides of the probe casing.

In this case it is particularly advantageous to provide means for automatically recognizing the type of array of transducers and/or the type of wireless communication means that are used.

Such recognition means can be composed of a logic execution program loaded within the processing unit and for example they can allow the several transducer arrays to be recognized by means of the possible types of connection, such as the number of pins, provided in the first and/or second part of the plug connectors. As an alternative the several transducer arrays and/or the communication means can transmit different signals when connected to the remaining part of the probe.

In both the cases once the different types have been recognized, the automatic recognition means regulate the processing circuit according to different operational parameters depending on the type of transducer array and/or of the communication means that is connected.

Therefore the present invention relates also to a kit comprising an ultrasound probe, having the operating and constructional characteristics that have been described above and the characteristics that will be described below, and at least two different removable transducer arrays and/or at least two different removable wireless communication means.

An improvement of a probe according to the present invention provides at least a part of the contacts provided at the side of the transducer array and/or at the side of the wireless communication means to be connected to the connector of the board on the opposite face of the frame. This allows communication lines between the electronic circuits of the two boards to be formed such that signals can be transferred from one board to the other one.

Preferably the power generating and storing source provided within the housing space formed by the two boards and by the means supporting them, is a rechargeable battery and it is mounted such that it can be removed from the probe. Even in this case the above described plug connectors are used for connecting the battery to one or both the boards, the contacts of one of the two parts of the plug connector being provided on the battery, while the contacts of the second part are provided on one or both the boards.

Moreover it is necessary to use interface means allowing the probe and/or the battery to be connected to an external power source, which are composed of plug connectors of the above described type, and a recharging electronic circuit. According to a first variant embodiment the recharging electronic circuit is mounted on the boards together with the interface means connecting such circuit to an external power network and allowing the battery to be recharged due to the connection of the battery to the two boards.

As an alternative the recharging electronic circuit is a circuit outside the probe directly connected to the battery through the interface means that allows the battery to be recharged independently of the probe. Such variant, in the case the battery is dead, allows the battery to be replaced by a back-up battery without preventing the probe from being used, and the battery from being recharged.

It is also possible to provide the recharging means to be composed of electromagnetic induction recharging means such to allow the battery to be recharged in a wireless mode.

The remote unit to which an ultrasound probe according to the present invention transmits the signals through the wireless communication means has communication means therein by means of which it transmits and receives the signals and it has a display device for displaying the video signal resulting from the processing made by the processing unit of the probe.

According to a variant embodiment inside the remote unit there is provided a unit allowing the received signal to further processed, such unit is composed of processor means that execute a logic program processing, transmitting and receiving signals and a storage unit intended to store the program, the data for executing the program and the data resulting from the execution.

As said above there are provided interface means belonging to the remote unit, which are composed of a user interface allowing the scanning parameters to be manually controlled; such interface communicates with the wireless communication means by sending control signals and/or codes for programming and setting the operational conditions of the processing and generating units of the probe.

An alternative example of the present invention provides the remote unit to have two or more communication channels for transmitting and receiving signals to two or more probes. In this case each probe has to be recognized by the remote unit, such to assign to different channels different probes, thus each probe can be for example univocally identified by an identification code or the probes can have communication channels with a predetermined bandwidth and centered on different frequencies, such to diversify the signals received or transmitted by different probes.

Independently of the number of probes used, the communication, display and further processing means of the remote unit are in common to all the probes, thus it is necessary to provide a method for diversifying the use of such means depending on the probe that is desired to be used. If probe is identified by an identification code, it is necessary for the remote unit to have processing means therein which have comparing tables for relating each probe to its own identification code and which activate one probe or another for the transmission and the reception. As an alternative there are provided switching means that alternately activate the transmission channels of the remote unit relating to frequencies at the bandwidths on which the transmission channels of the different probes are centered.

Advantageously the communication, display and further processing means of the remote unit, are in common to all the probes, since the fact of sharing such means in combination with the storage units provided into the storage unit allows the signals received and transmitted by the different probes to be processed many times, for example, it being possible to alternately or contemporaneously display the different images that then can be compared, modified and/or corrected.

The method applied in the preferred embodiment of the present invention is different from the prior art.

With reference to the prior art such methods provide said transmitting transducer array to send a focused or non-focused ultrasound beam and provide said receiving transducer array to receive the echoes reflected by the structures of the body under examination.

At least a part of the transmitting transducers can be used as receiving transducers and vice versa, alternating transmitting and receiving phases over time.

According to some of the most used operating modes, the focused beam penetrates into the body under examination along lines of sight, that is lines of propagation that arise at the transmitting transducers and develop into the body under examination following the direction of propagation of the wave front, defining a scan plane or slice.

Such lines of sight can be parallel one another or radially arranged depending on the relative geometrical arrangement of the transmitting transducers and of the excitation modes of the transmitting transducers.

Similarly the reception by the receiving transducers occurs by means of such lines of sight such that each receiving transducer receives information from the reflected echoes with reference to a sector of the scan plane defined by the line of sight generated by the propagation of the wave generated by a following transmitting transducer or from the transducer used for the transmission.

According to a particular method known by the name of compound imaging, several ultrasound beams penetrate into the body under examination according to different points of the transmitting transducer array and the reflected echoes are detected in the reception phase and are transformed into images that later can be combined one another.

The drawback of such method is that the frame-rate is reduced, such reduction increases as the images generated by different observation points increase.

In an alternative embodiment the waves penetrate into the body under examination in a non-focused way or defocused way such that it results in a beam with a wide aperture and the scan slice is largely insonated.

In the reception phase each transducer detects a reception signal on which it is necessary to apply windows with specific time shifts depending on the distance of the receiving transducer from the transmitting transducer and from the transmission point in the body under examination in order to gain information concerning the wave reflected by such transmission point in the body under examination.

This mode has the drawback that, since the beam is not focused, the introduced acoustic energy is spread into a wider area and therefore each reflection point in the body under examination is impinged by a wave having a lower intensity.

This leads necessarily to echoes having a reduced intensity and therefore to an inevitable reduction of the signal to noise ratio in the reception signals.

The above drawbacks are overcome by the present invention and, in addition to an apparatus, the present invention relates also to a method for acquiring ultrasound images according to the general embodiment and/or to the specific embodiments that have been described above.

A method according to the present invention therefore allow a univocal definition of a grid of reference points having predetermined positions on the scan plane, by means of which it is possible to precisely define the relative distances between the various points of the scan plane and the transducers.

The distance of each point of the grid from each transducer is known, and, since the propagation velocity of the acoustic wave in the body under examination is known and substantially unchanging, once the space distance is known it is possible to univocally define the time when a wave reflected by any reflection point arranged on the grid impinges on any transducers.

This means that the acoustic wave transmitted from a specific transducer impinges on a reflection point after a predetermined time, it is reflected by such reflection point and returns back in the opposite direction towards the transducer.

The transducer that has transmitted the ultrasound pulse detects the echo reflected after a time that is twice the time that the transmitted wave takes to reach the reflection point.

The receiving transducers arranged at the sides of such transducer used both for the transmission and the reception, receive the reflected wave after a time different than the initial transducer, and the time shift is due to the relative arrangement of the transducers and their distance, the distance of each transducer from the reflection point deriving therefrom.

In an example case that provides a linear probe, the receiving transducers that are arranged at the sides of the transmitting transducer receive the reflected signals after a time delay At that is directly proportional to the distance between each transducer of such receiving transducers and the transducer that has transmitted the pulse.

Thus it is possible to obtain for each transducer the components of the reception signal containing information coming from the reflection signal of a predetermined reflection point in the body under examination, by applying suitable windows to the reception signal, which are shifted over time according to the appropriate delays.

In theory, due to the fact of having high velocity components, it would be possible to make the calculation of all the points of the image in the time between a transmission and another; in practice it is sufficient to have all the data of each element in the storage and to make the calculation in a time shorter than 1 ms.

By combining such components of the reception signals of all or at least of a part of the reception signals, which components of the reception signals each one holds information coming from the reflection signal of the same reflection point in the body under examination, it is possible to generate images with acceptable resolutions, while considerably increasing the frame-rate, since a non-focused transmission is enough for receiving echoes on all or a part of the receiving transducers.

A method according to the present invention has the further advantage of providing additional transmissions after the first one, and of combining all the obtained images, particularly calculating a mean, in order to obtain a final image that optimizes the contributions of all the images obtained from different transmitting points.

The generation of said grid of points on the scan plane, that defines lines parallel to the direction of propagation of the acoustic wave that can be parallel each other or diverging depending on the shape of the body section to be displayed, and that can define cells between reflection points of any shape, for example square or rectangular shapes, has the advantage of allowing a high number of images to be combined in a short time, since the distances are known a priori.

By means of this it is also possible to obtain images that can be already overlapped one another, such that a further adjustment and processing are not necessary, thus considerably saving time.

In a preferred embodiment the image frame-rate is more than 1000 frame/sec, but it is possible to combine the obtained images even every 20-30 ms, if the computing power is not sufficient.

According to an embodiment the image is generated along the scan plane or slice of the body under examination by the mean of the reflection signals of the sets of reflection signals generated by the individual spherical transmission pulses transmitted by the several transmitting points.

In a variant embodiment said sum or said mean of the reflection signals of the individual sets of reflection signals is separately calculated for each one of the reflection points, that is the sum or mean is calculated from the values of the reflection signal of each reflection point as stored in the various sets of reflection signals.

According to such embodiment said sum or mean of the reflection signals is calculated upstream of conversion into image data by said processing means.

In an alternative embodiment the reflection signals of the individual sets of reflection signals are converted into image data and then separately stored, for each set of reflection signals, said sum or mean being calculated using the image data deriving from the individual sets of reflection signals.

According to a further embodiment the determination of a sub-grid smaller than said grid is provided, whose peripheral points coincide with at least part of the points of said grid and that is formed of as many points as those contained in said grid, in the area delimited by the peripheral points of said sub-grid or more.

This defines a region of interest into an obtained image, thus allowing the following acquisitions to be made in such region of interest.

This is possible by defining the sub-grid, with the relevant recalculation of the points constituting it.

In a preferred embodiment the number of points in the sub-grid is the same as the points of the grid, since it is optimized for the computing power of the processing means.

In an alternative embodiment the transmitting transducers and the receiving transducers used for scanning are provided in a number smaller than the total amount and are limited to a reduced area surrounding or near the region of interest wherein said sub-grid is defined.

As it is known to the person skilled in the art, the transmitting transducers can also be the receiving transducers they being actuated alternately for the transmission and reception of acoustic signals.

In a further embodiment the processing means comprise means for forming and focusing an acoustic beam on the individual reflection points the so called receive/transmit beamformers.

In a further embodiment the array of transmitting and receiving transducers is a two-dimensional array, said array of transducers generating scan volumes for the body under examination where acoustic pulses are transmitted and from where the reflection pulses of the transmitted acoustic pulses are received.

In this case the predetermined reflection points are arranged in a three-dimensional grid within the scan volume, the transmitting points are arranged along the two-dimensional surface of the array of transmitting transducers and each set of reflection signals comprises the reflection signals of the reflection points of the three-dimensional grid of the reflection points for forming a three-dimensional image.

The invention relates also to other features, further improving the above apparatus and method, which are also objects of the claims.

BRIEF DESCRIPTION OF THE DRAWINGS

These and other characteristics and advantages of the present invention will be clearer from the following description of a few embodiments shown in the annexed drawings, wherein.

DETAILED DESCRIPTION OF EMBODIMENTS OF THE INVENTION

With reference to FIGS. 1 to 6, an apparatus according to the invention has the shape, dimensions and weight typical of currently known ultrasound probes. Therefore, in the following description the term probe is to be understood as a synonym for the term apparatus for ultrasound image acquisition unless a different meaning is specifically given within a specific context.

In one embodiment, the illustrated ultrasound probe is composed of an outer casing 1 comprising two narrow and longer side faces and two wider and longer faces, parallel to each other and oriented lengthwise in the direction of a longitudinal axis along the direction of propagation of the acoustic beam transmitted from the probe. Moreover, there are provided two boards 11 and 12, which are parallel or substantially parallel to the wider faces. The units generating and processing the transmitted and/or received signals, as well as the circuits powering the units, are arranged on such boards 11 and 12.

An array of electro-acoustic transducers 3 is fastened at one of the two ends of the boards 11 and 12. Each of the transducers transmits ultrasound waves when powered with an electric excitation signal and also generates an electric reception signal when impinged by an ultrasound wave or pulse that can be generated by the reflection of ultrasound waves transmitted from the same transducer.

Advantageously, but not exclusively, the array of transducers 3, at the side composed of the ultrasound transmitting surfaces 32, is covered with at least one matching layer, intended to match the acoustic impedance of the array of transducers 3 to that of the body to be examined, in order to avoid abrupt changes in the acoustic impedance that would produce reflection surfaces that would prevent the ultrasound beam from penetrating into the body under examination.

Figure 1:
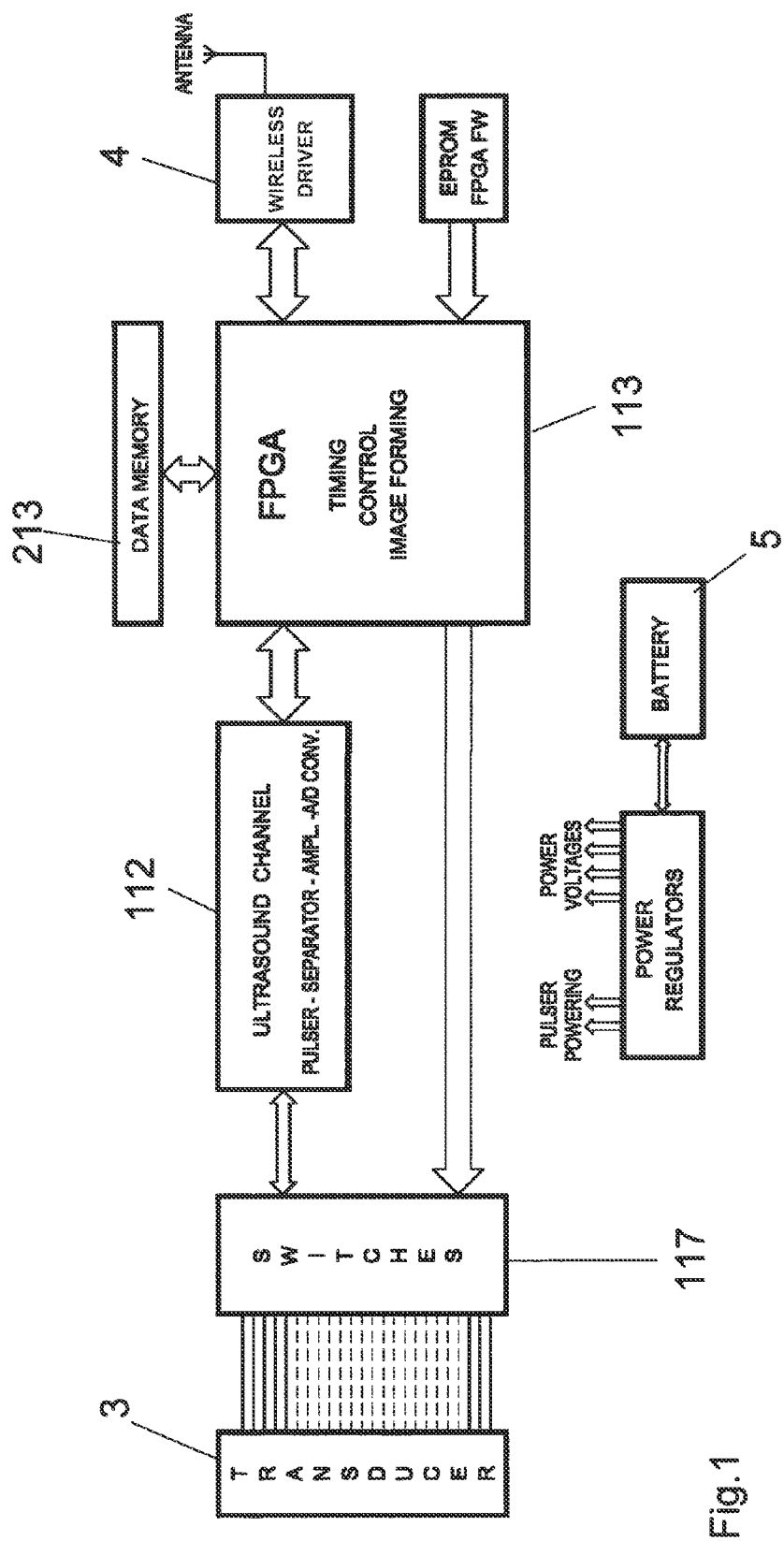
FIG. 1 is a schematic diagram of the various components of an apparatus according to the invention, where image scanning and forming means are integrated in a typical ultrasound probe.
Figure 2:
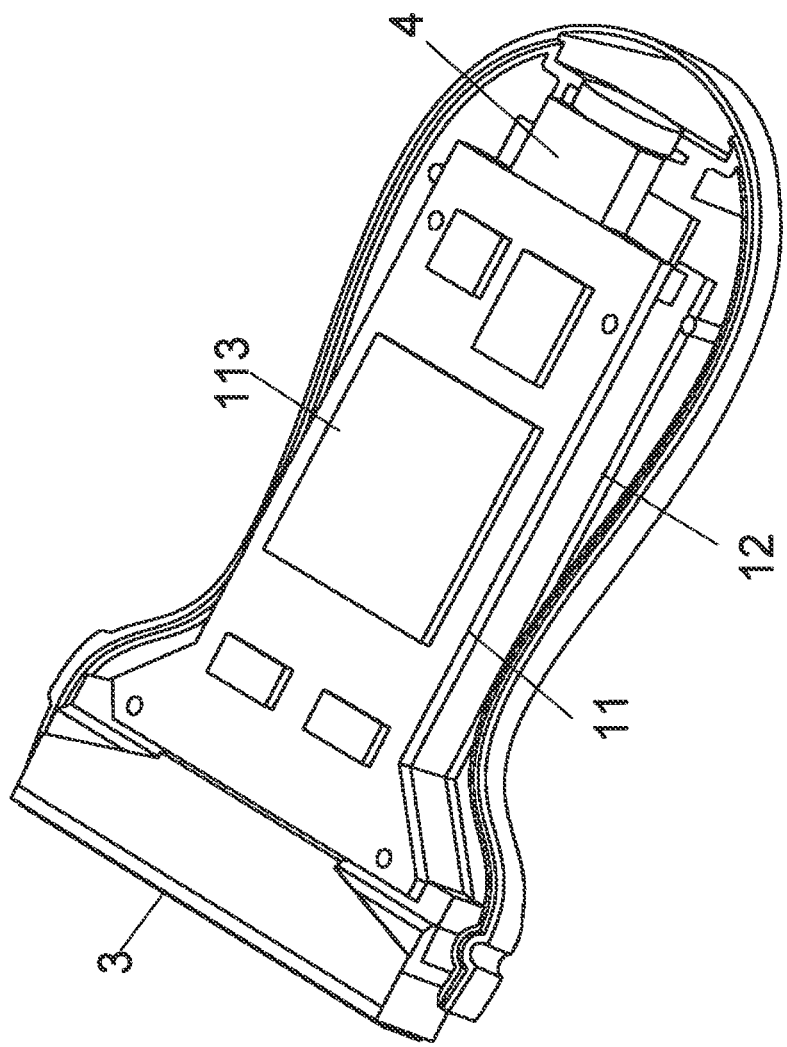
FIG. 2 is a view of an apparatus according to the invention, with a particular reference to the upper board.
Figure 3:
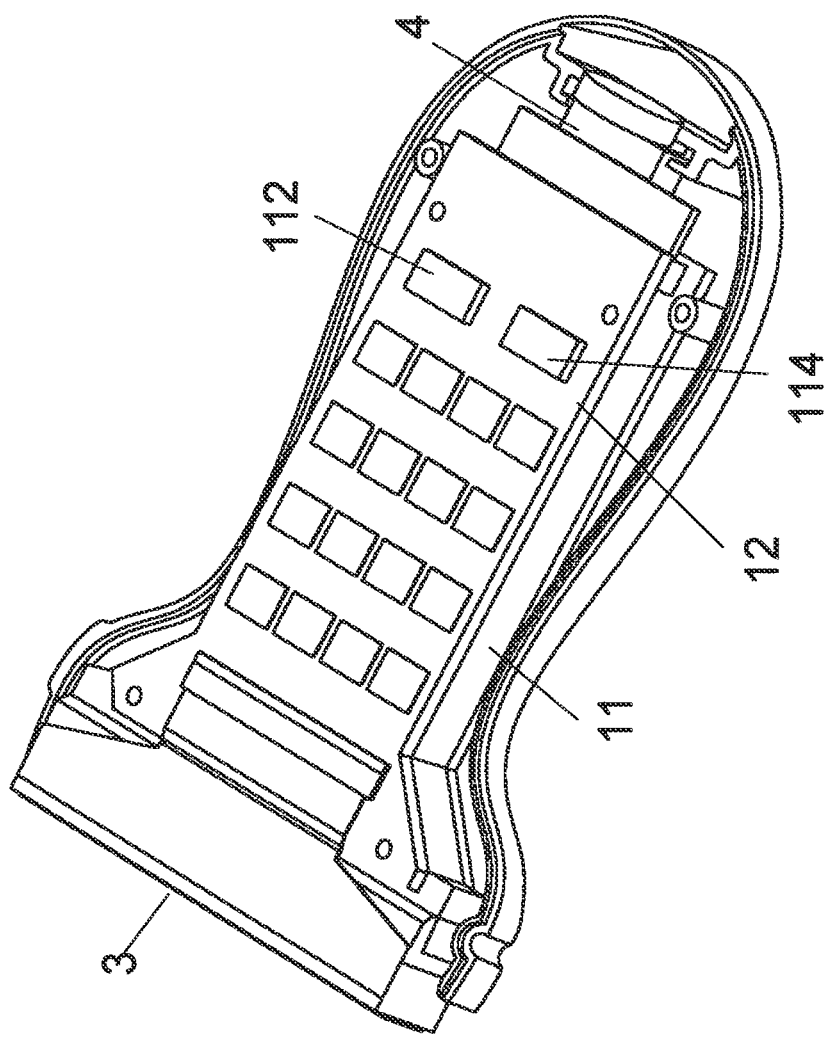
FIG. 3 is a view of an apparatus according to the invention, with a particular reference to the lower board.
Figure 4:
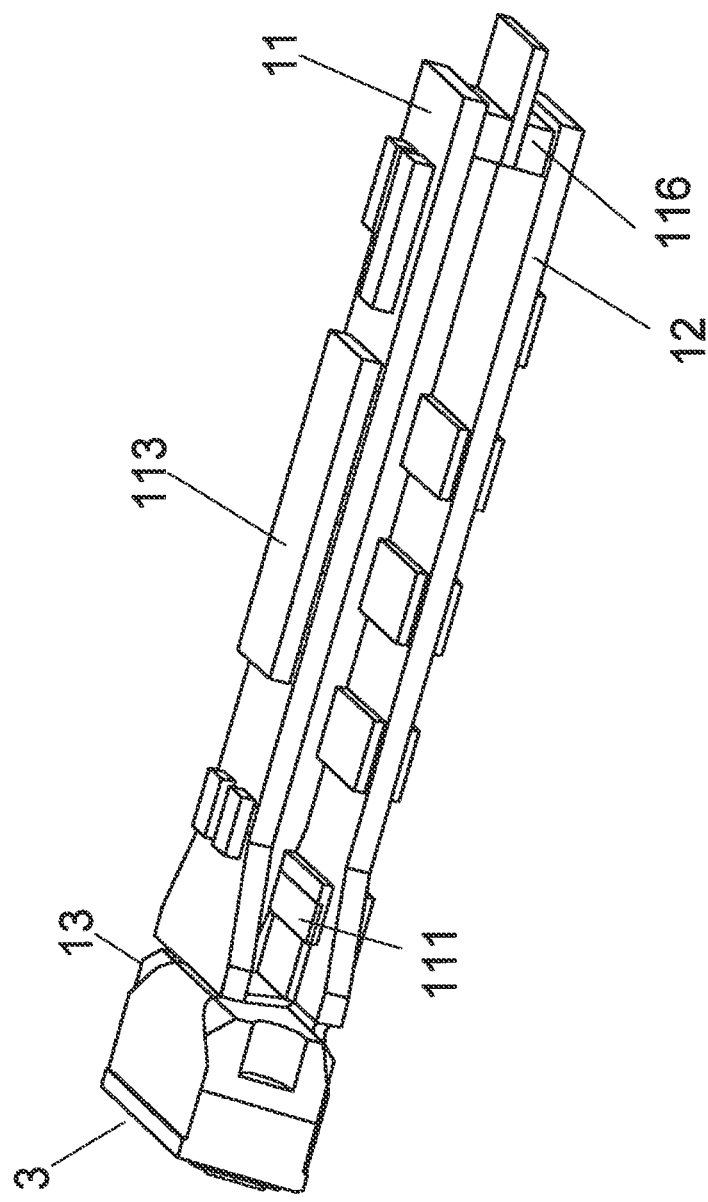
FIG. 4 illustrates an arrangement of the boards and the connection of said boards with the array of transducers and with the wireless communication means.
Figure 5:
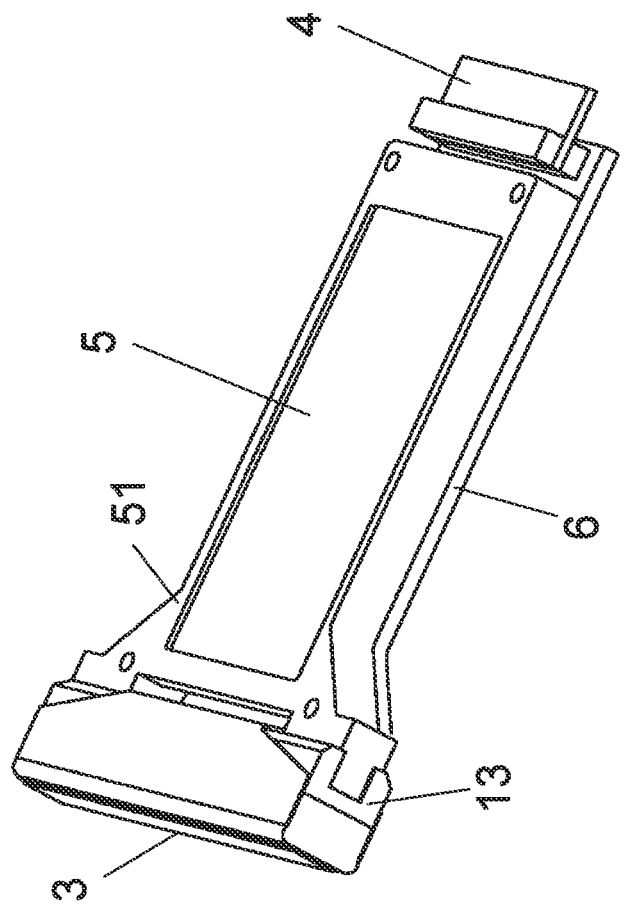
FIG. 5 is a view of an apparatus according to the invention, with a particular reference to the battery and the frame supporting the two boards.

The array of electro-acoustic transducers 3 is connected to the boards 11 and 12 by means of plug connectors 111, a first part of which cooperates with a corresponding second part. In FIG. 4 they are oriented with the connection contacts in the longitudinal direction with respect to the probe, such to be coupled and uncoupled by a movement in that direction.

The contacts of the first part of the plug connector 111 are fastened to inputs and/or outputs respectively of the array of transducers 3 and the contacts of the second part are at the ends of the two boards 11 and 12, such that the transducer array 3 is connected with the means generating 112 and processing 113 the transmitted and/or received signals. A storage area 213 is associated thereto, whose task will be described below with reference to particular image scanning and forming modes of the preferred embodiment.

The embodiment illustrated in FIGS. 1 to 6 provides for the use of mechanical engagement means 13 intended to fasten the transducer array 3 to the probe casing.

The generating unit 112 generates excitation signals that are transmitted, through the plug connectors 111, to the transducer array 3 and comprises means generating the excitation signals and means feeding the signals to the individual transducers.

In one embodiment, the generating unit 112 sends time-varying frequency excitation signals. The transmitted ultrasound pulses are encoded by frequency variations over time according to a specific function over time, such as, for example, a linear or non-linear function. Particularly, so called "CHIRP" signals may be generated, whose frequency variation over time allows the number of communication lines between the transducer array and the signal generating unit 112 and processing unit 113 to be drastically reduced.

To this end, each transducer of the transducer array 3 is connected to the processing unit 113 and to the generating unit 112 by a switch 117, which has two conditions, an operating condition, enabling each transducer to receive/transmit electric excitation signals, and a non-operating condition, disabling each transducer from receiving/transmitting electric excitation signals, respectively. The transition from the operating condition to the non-operating condition is set by the processing unit 113 that alternates the reception/transmission of each individual transducer according to specific time sequences different for each individual transducer of the transducer array 3.

Each transducer of the transducer array 3 generates a reception signal that is transmitted to the processing unit 113 through the plug connectors 111.

The unit 113 further comprises means for converting the reception signals into image data, as well as video signal generating means. The reception signal processed by the processing unit 113 as an output from the unit itself is therefore converted into a video signal.

With particular reference again to FIGS. 1 to 6, the processing unit 113 is composed of a FPGA device (Field Programmable Gate Array) provided in combination with an analog/digital converter 114, which converts the input signals of the FPGA device into digital data such that they can be processed by said device, and with a storage or a plurality of storages generally denoted by 213, whose tasks will be described in greater detail below.

The video signal provided as output from the processing unit 113 is sent to the wireless communication means 4 that allow video signals to be transmitted and allow an ultrasound probe according to the invention to communicate with a remote display, storage and additional processing unit (not shown).

Communication means 4 are connected to the other end of the boards 11 and 12 by plug connectors 116, a first part of which cooperates with the corresponding second part. Boards 11 and 12 are connected to each another in an engaging/disengaging direction perpendicular to the direction of propagation of the beam and perpendicular to the surface of the boards 11 and 12, such that the boards 11 and 12 are mounted in connection with the wireless communication means 4.

The contacts of the first part of the plug connector 116 are fastened to the inputs and/or outputs respectively of the communication means 4 and the contacts of the second part are at the ends of the two boards 11 and 12, such that the wireless communication means 4 are in connection with the means 112 generating and with the means 113 processing the transmitted and/or received signals.

Moreover, in the embodiment shown in the FIGS. 1 to 6, an ultrasound probe according to the invention provides for the use of means for powering electronic circuits, which are composed of a power generating and storing source, such as a battery or the like 5, provided in combination with and connected to circuits matching and connecting the battery to the processing and generating units 113 and 112, and to the wireless communication means 4.

In an alternative embodiment, at least a part of the contacts provided at the side of the transducer array 3 and/or at the side of the wireless communication means 4 is connected to the connector of the board on the opposite face of the frame 6. This allows communication lines among the electronic circuits of the two boards 11 and 12 to be formed such that signals can be transferred from one board to the other one.

The battery 5 is arranged in a housing space 51 that is composed of a frame supporting the two boards 11 and 12.

Figure 6:
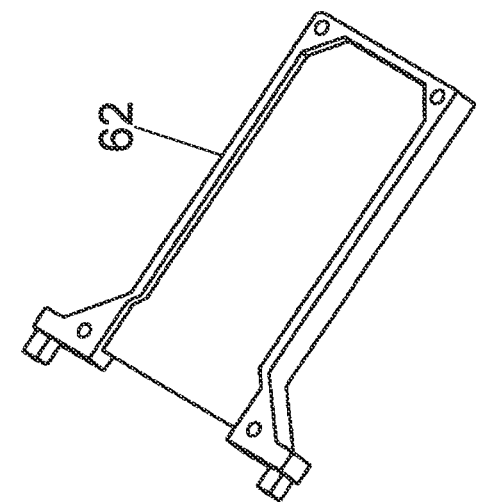
FIG. 6 illustrates means supporting the boards.
Figure 6:
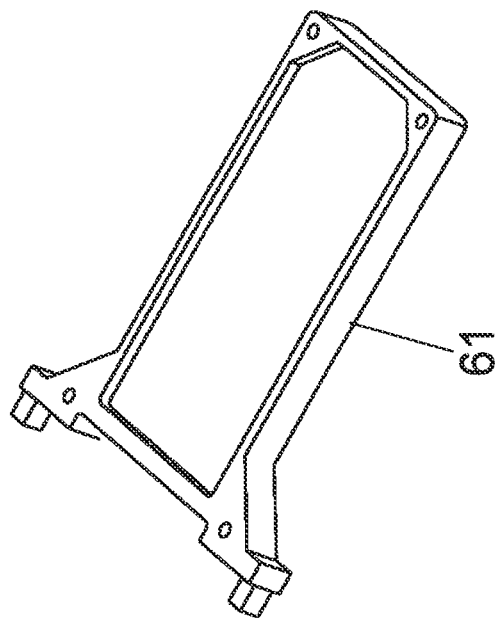

The boards 11 and 12 are supported by supporting means 61 and 62, which allow the boards 11 and 12 to be arranged parallel each other, and allow also a housing space 51 for the battery 5 to be made. The supporting frame 6, composed of the supporting means 61 and 62, spaces apart the boards 11 and 12 and allows the battery 5 to be housed within the space between the two boards. In FIG. 6, the frame 6 is composed of a peripheral rim having a thickness substantially corresponding to the thickness of the battery 5 and/or to the gap between the two boards 11 and 12. Such rim delimits a central space 51 between the two boards 11 and 12 for housing the battery 5. A plate may be provided, not shown in FIG. 6, closing at least one of the open sides of the frame 6 that allows the frame 6 to rest on the plate such to form the bottom of the housing space 51 comprising the contacts for the connection between the battery 5 and the boards 11 and 12, such to power the generating unit 112 and the processing unit 113.

Preferably, the power means and the generating unit 112 and the processing unit 113 are made in the form of printed electronic circuits on the two boards 11 and 12, which are fastened to the frame 6 and are oriented parallel to the larger faces of the probe casing.

Advantageously, the battery 5, provided inside the housing space 51 composed of the two boards 11 and 12 and of the supporting means 61 and 62 thereof, is a rechargeable battery and it is mounted so as it can be removed from the probe. Even in this case the above described plug connectors 111 and 116 are used for connecting the battery 5 to one or both the boards 11 and 12. In this configuration, the contacts of one of the two parts of the plug connector will be on the battery 5, while the contacts of the second part will be on one or both the boards 11 and 12.

Moreover, it is necessary to use interface means, which allow the probe and/or the battery 5 to be connected to an external power source, and which are composed of plug connectors of the described above type and a recharging electronic circuit. In one embodiment, the recharging electronic circuit is fitted on the boards 11 and 12 together with the interface means that connect such circuit to an external power network and allow the battery 5 to be recharged by means of the connection of the battery 5 to the two boards 11 and 12.

As an alternative, the recharging electronic circuit is a circuit outside the probe directly connected to the battery 5 by the interface means allowing the battery 5 to be recharged independently of the probe. If the battery 5 is dead, such variant allows the battery to be replaced by a back-up battery without preventing use of the probe and recharging of the battery.

The recharging means may also be composed of electromagnetic induction recharging means such to allow the battery 5 to be recharged in wireless mode.

Figure 7:
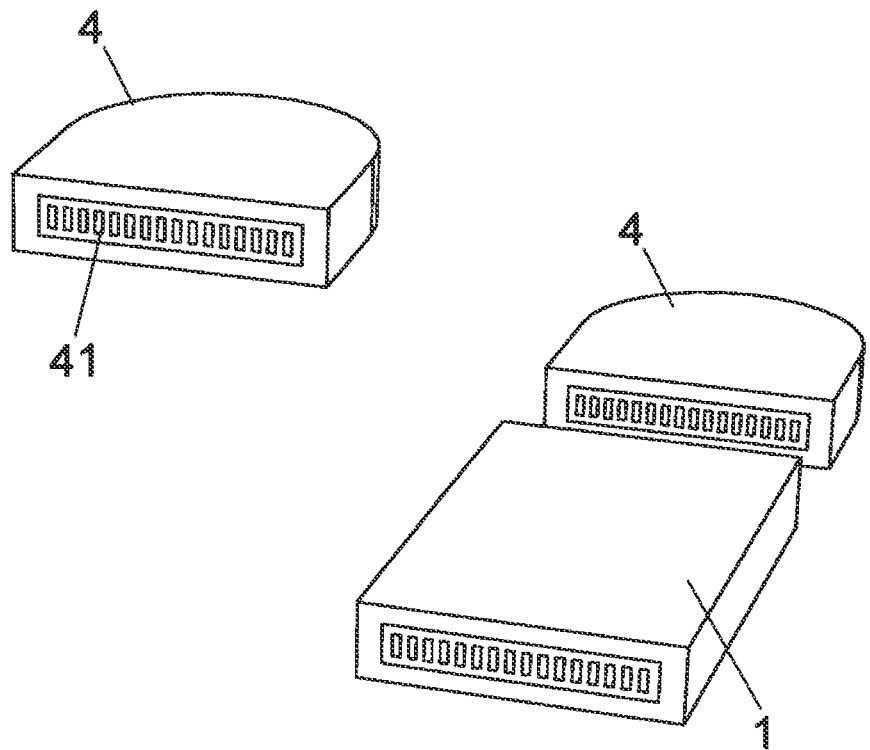
FIG. 7 illustrates a kit according to the present invention.
Figure 7:
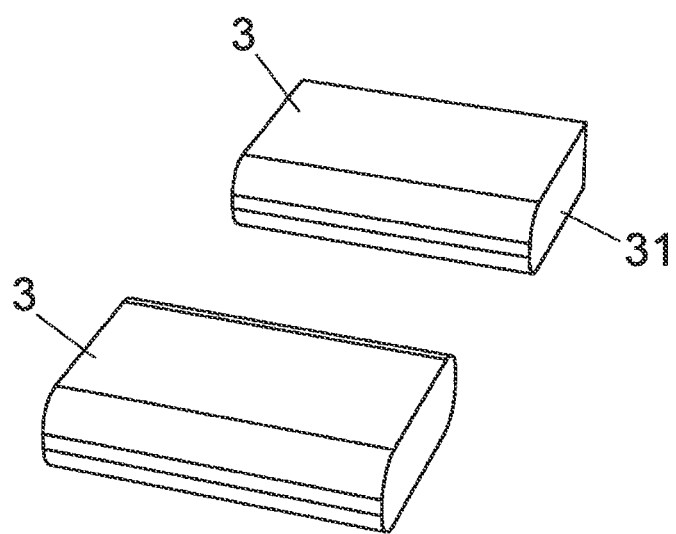

FIG. 7 shows a kit according to the invention comprising an ultrasound probe, having the above described constructional and operational characteristics, and at least two different removable transducer arrays 3 and/or at least two different removable wireless communication means 4.

FIG. 7 shows also a variant embodiment of the invention providing for the transducer array 3 and the wireless communication means 4 to be removably mounted onto the structure of the probe 1, such that different transducer arrays and different communication means can be used while keeping the same control electronics.

The transducer array 3 and the communication means 4 can be mounted or removed by means of the above described plug connectors, which are made as electric/mechanical connection means composed in turn of a first part of a plug connector cooperating with a corresponding second part of a plug connector 111, 116, with the first part fastened to the inputs/outputs of the transducer array 3 and to the input/outputs of the wireless communication means 4 respectively, and with the second part fastened to the ends of the casing of the probe 1 holding the control electronics.

Within such control electronics there are provided means, not shown in FIG. 7, for automatically recognizing which type of transducer array 3 and which type of wireless communication means 4 are used.

Such recognition means can be composed of a logic execution program loaded within the processing unit 113, and, for instance, can allow recognition of the different transducer arrays 3 by means of the possible types of connection, such as the number of pins 31, 41 provided in the first and/or second part of the plug connectors. As an alternative, the different transducer arrays 3 and the communication means 4 can transmit different signals when connected to the remaining part of the probe.

In both the cases, once the different types have been recognized, the automatic recognition means regulate the processing circuit 113 according to operating parameters, which are different depending on the type of transducer array 3 and/or of the communication means 4 that are connected.

Finally, it has to be noted that the above described probe can be associated to any type of device intended to generate a synergy from a functional point of view with the probe. An example could be represented by means automatically recognizing a user, such as a fingerprint scanner, that allow, through the use of databases, the user to be automatically recognized and the type of examinations that such user can perform to be verified by automatically setting specific operating parameters of the probe and of the remote display unit.

Figure 8:
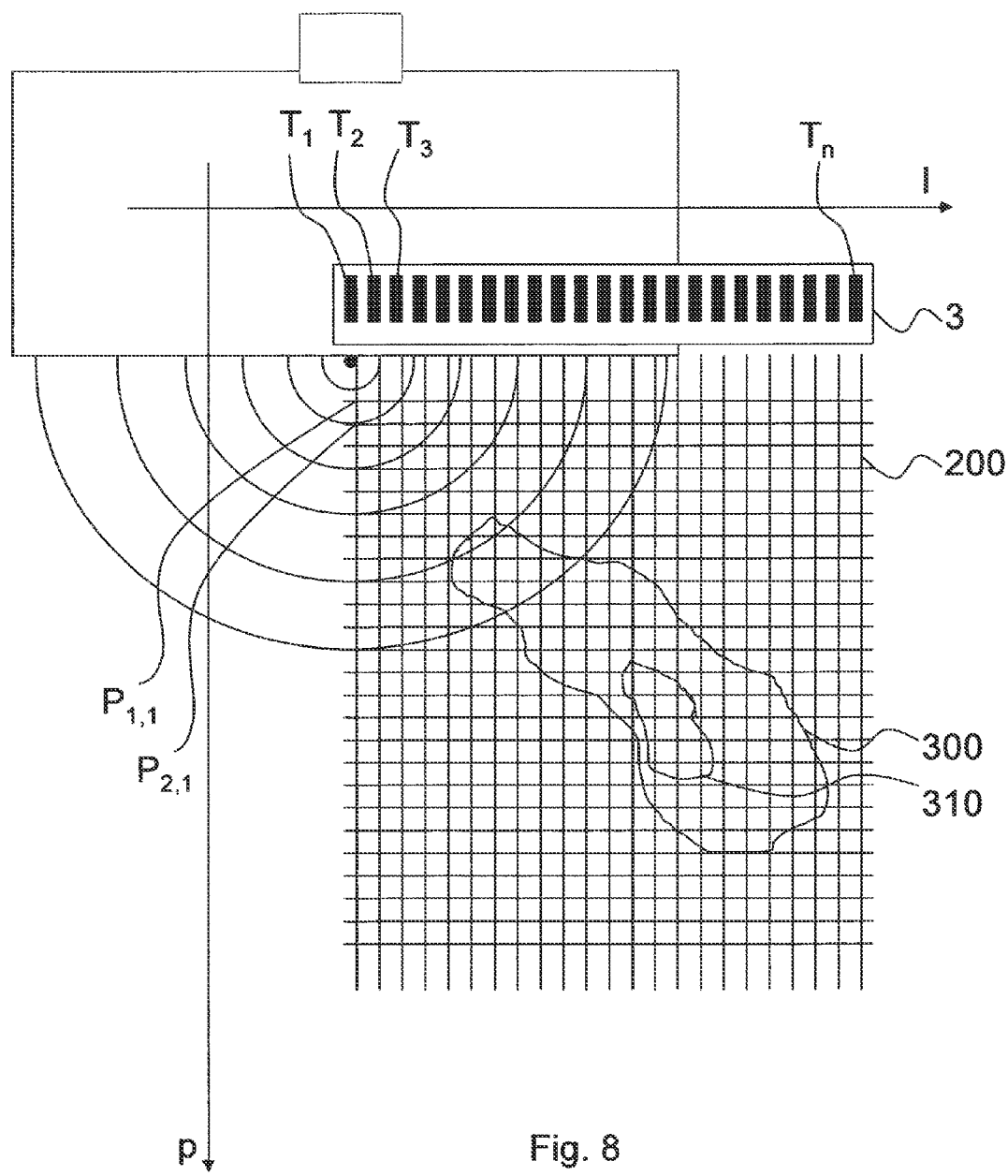
FIGS. 8, 9 and 10 are schematic and simplified views of the transmission of ultrasound pulses by different transmitting points.
Figure 9:
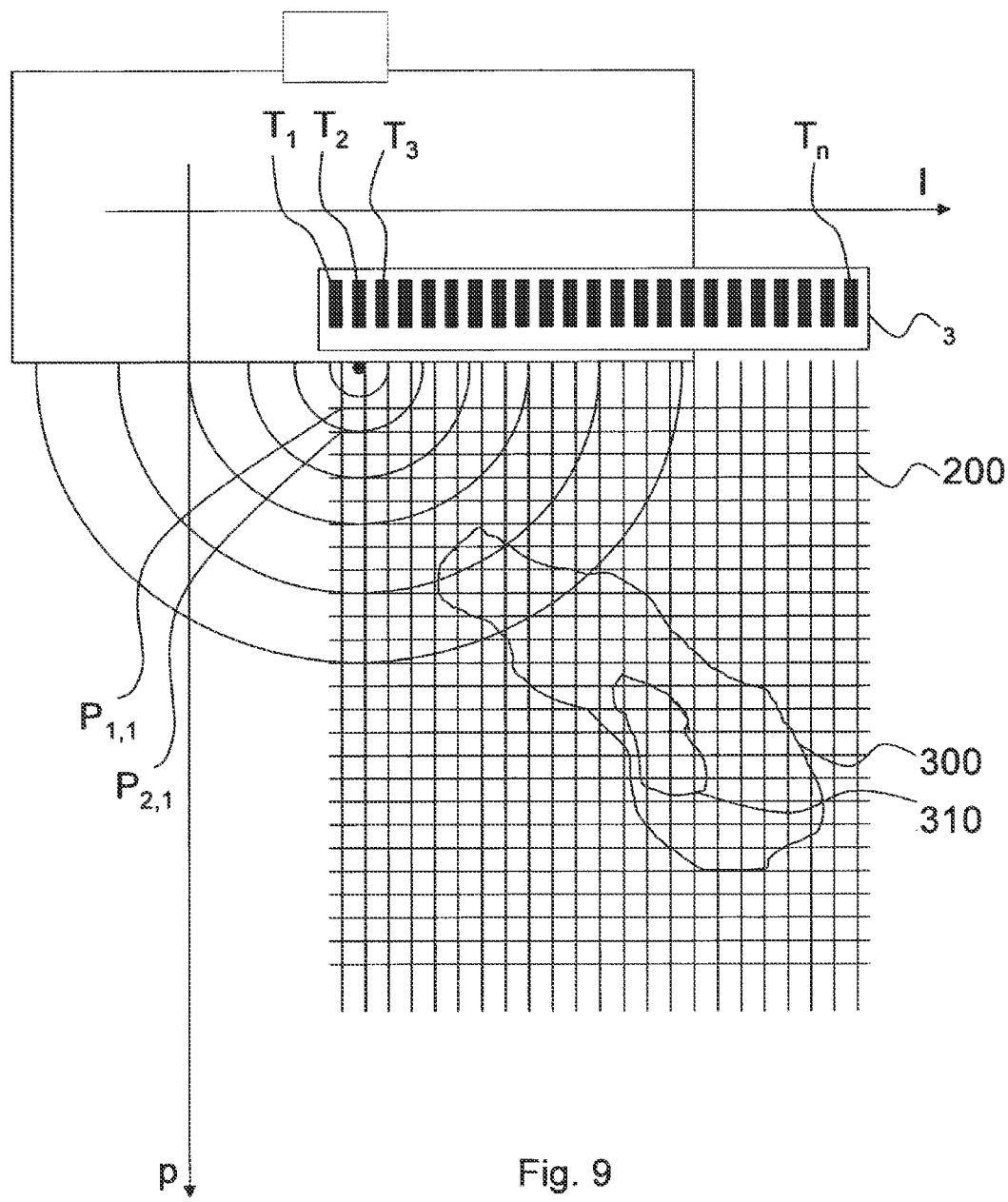
Figure 10:
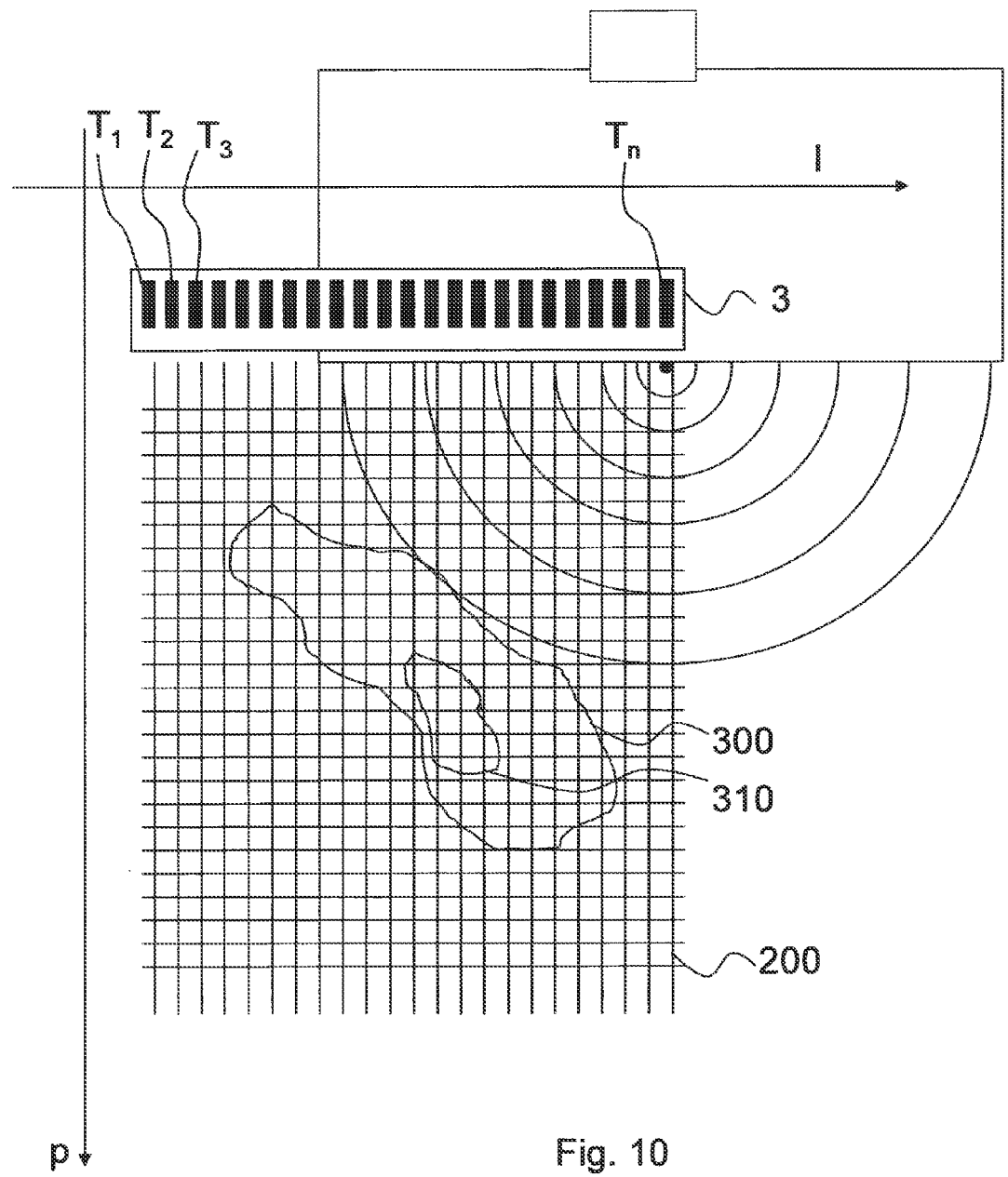

FIGS. 8, 9 and 10 as well as other figures show in greater detail the structure and the operating modes of the processing means with a particular reference to means generating the excitation signals, to means activating the transducers for the reception, and to the mode for forming the image starting from received data. In FIGS. 8, 9 and 10 there is shown a transducer array 3 comprising the transducers $T_1, T_2 \ldots T_n$, arranged according to a system of Cartesian axes l and p, where l is the width of the transducer array 3 and p is the depth into the body under examination.

At least a part of the transmitting transducers can be used as receiving transducers and vice versa, by alternating the transmission and reception phases over time.

In the embodiment shown in the figures, the transducer array 3 is used both for transmission and reception.

A set of predetermined reflection points $P_{1,1} \ldots P_{n,n}$ is defined which are arranged at a predetermined distance from each other and form a grid 300 extending in the scan plane or slice along which the body under examination is imaged.

Such grid can define cells having any shape, for example square or rectangular shapes, between reflection points.

The individual transducers successively transmit an ultrasound transmission pulse in the form of a spherical wave from each of a plurality of transmitting points all along the extension of the array of transmitting transducers toward the body under examination which defines a scan plane or slice, where anatomical structures of interest 300, 310 are provided.

Such successive transmission of an acoustic pulse in one embodiment occurs by each transducer $T_1, \ldots T_n$ of the transducer array 1, such as that shown in FIGS. 8, 9 and 10, wherein FIG. 8 shows a first transmission of the acoustic pulse by the transducer $T_1$ placed at a first end of the transducer array 3, FIG. 9 shows a second transmission by the transducer $T_2$ immediately following the transducer $T_1$, and FIG. 10 shows a last transmission by the transducer $T_n$ arranged at a second end of the transducer array 3, such to show that each transducer in the array of transducers 3 has made a transmission that is made successively starting from said first end of the transducer array 1 to the second end.

It is possible to provide additional embodiments where only a part of the transducers performs a transmission, for example a transducer every two or three transducers or according to any different arrangement.

In particular, for example when the object to be examined is small with respect to the aperture of the transducer array, it is possible to provide the transmission only by one subset of transducers of the array. The subset has a number of transducers smaller than the total number of transducers that are arranged directly adjacent one another, at least the first and/or the last transducer of the subset non coinciding with the first or the last transducer of the array respectively with reference to their arrangement in the transducer array.

It is possible to provide also two or more subsets of transducers of the transducer array. In this case each subset can comprise a certain number of transducers different from one subset to another, which are arranged in a direct adjacent relation or which are alternated to inoperative transducers or to transducers of another subset.

When, for example, the Field of View (FOV) of the probe include different objects that are spaced apart and that have dimensions smaller than said FOV, it is possible to provide two subsets of transducers, each intended to acquire an image relating to one of the different objects and therefore that image is generated by different transducers of the transducer array having a different position within the array.

A person skilled in the art can easily understand how any other combination of the transducers can be provided in order to transmit the transmission pulses depending on needs.

The transmitted acoustic pulses are reflected by the structural elements of the body under examination having acoustic reflector features and are received by said transducer array 3, such that each transducer generates a reception signal.

There are also provided processing means 113 to which each transducer is connected. Each transducer provides to such processing means 113 the electric reception signal generated by the excitation of said transducer upon reception of the reflected acoustic signal impinging upon said receiving transducer.

Each point of the grid 300 therefore generates a reflection signal corresponding to the structural features of a location in the body under examination that is situated precisely in that point.

Figure 11:
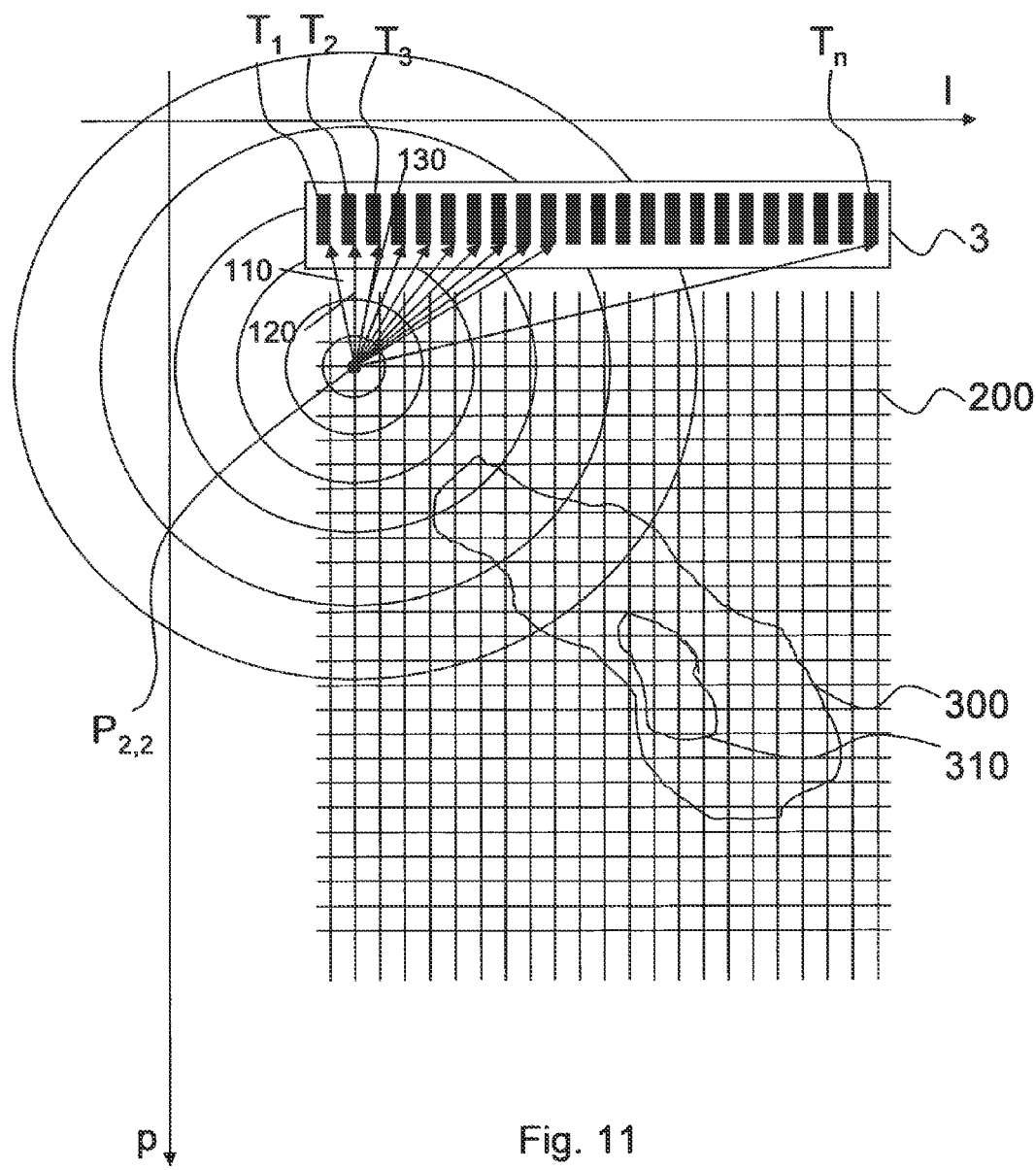
FIGS. 11, 12 and 13 are schematic and simplified views of the reflection of said ultrasound pulses by different reflection points on the grid.
Figure 12:
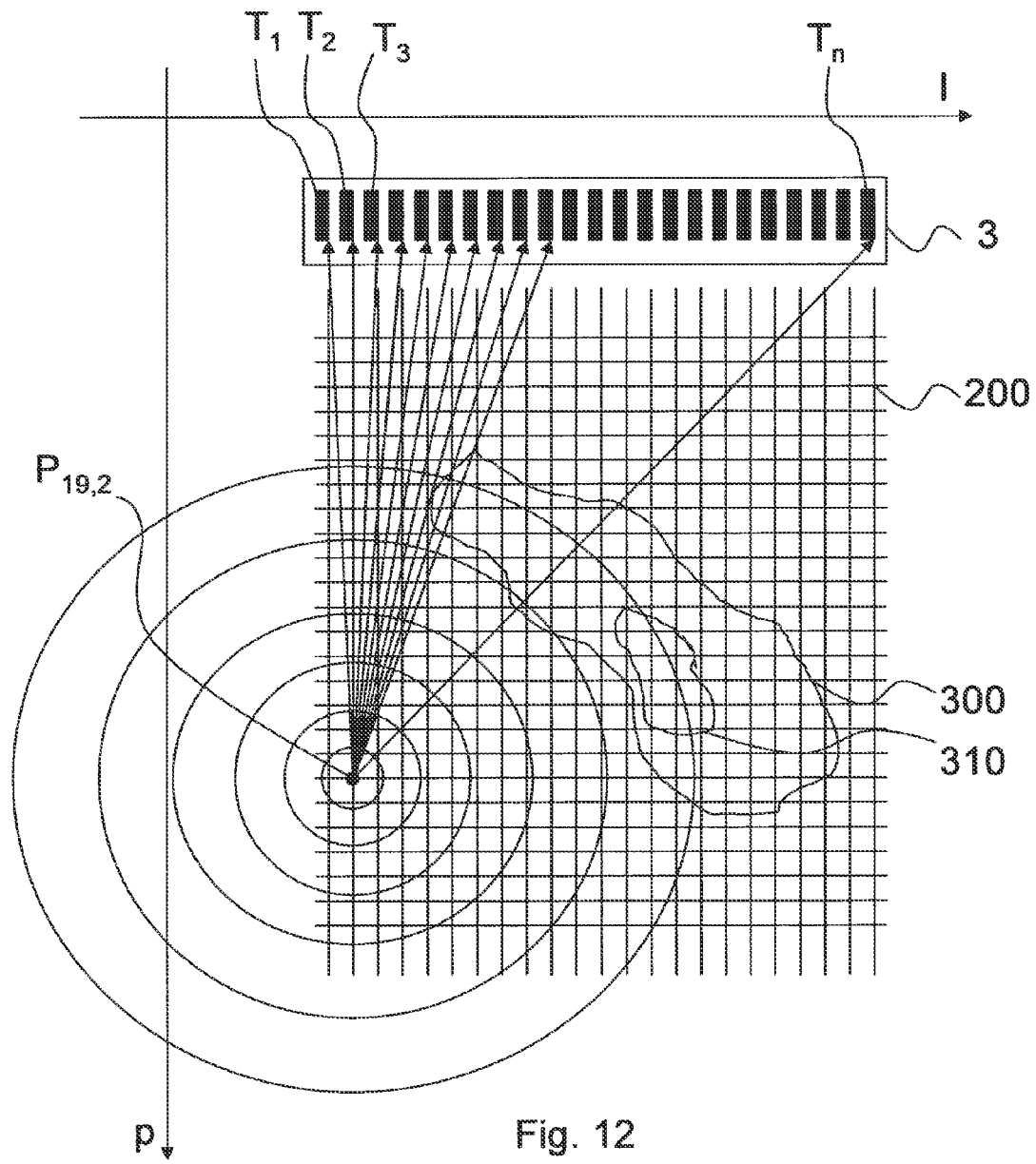
Figure 13:
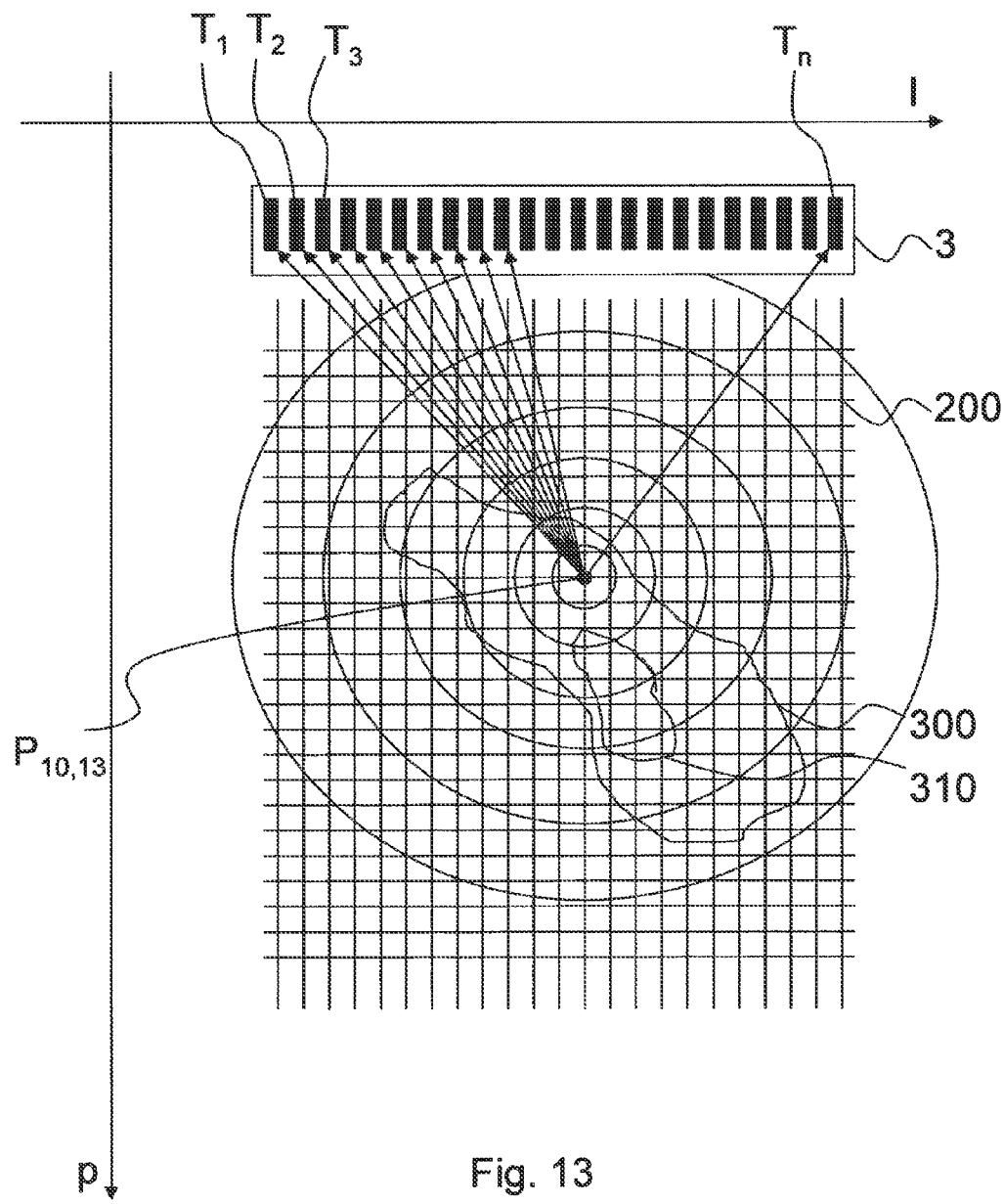

This can be clearly seen in FIGS. 11, 12 and 13, where reflection acoustic pulses generated by three different points of the grid 200 are schematically shown by way of example: $P_{2,2}, P_{19,2}$ and $P_{10,13}$. It will be appreciated that what is schematically shown for those three points is valid for each point of the grid of the reflection points.

The distance of each reflection point from each transducer is denoted by the arrows and corresponds to the time covered by the acoustic wave and therefore to the time shift of the signal components concerning the same point in the reception signal of each transducer.

The distance of each point of the grid from each transducer is known, and, since the propagation velocity of the acoustic wave in the body under examination is known and substantially unchanging, once the space distance is known it is possible to univocally define the time when a wave reflected by any reflection point arranged on the grid impinges on any transducers $T_1 \ldots T_n$.

This means that the acoustic wave transmitted from a specific transducer impinges on a reflection point after a predetermined time, it is reflected by such reflection point and returns back in the opposite direction toward the transducer.

Take FIG. 11 as an example and let the condition be after the transmission by the transducer $T_2$ shown in FIG. 9: the acoustic pulse is reflected by the point $P_{2,2}$ and it returns back toward the transducer array 3.

The transducer $T_2$, which has transmitted the ultrasonic pulse, detects the echo reflected by the point $P_{2,2}$ after a time that is twice the time that the transmitted wave takes to reach the reflection point and that corresponds to the distance denoted by the arrow 120.

The receiving transducers $T_1$ and $T_3$, arranged at the sides of the transducer $T_2$, receive the reflected wave after a time different than the transducer $T_2$, and the time shift is due to the relative arrangement of the transducers $T_1 \ldots T_n$ and to their distance, the distance of each transducer from the reflection point deriving therefrom.

In particular, the distances of $T_1$ and $T_3$ with respect to the point $P_{2,2}$ are shown by arrows 110 and 130 respectively, and the further distances of the additional transducers are shown by the further arrows, such that the transducers arranged at the sides of the transmitting transducer receive the reflected signals after a time delay $\Delta t$ that is directly proportional to the distance between each of such receiving transducers and the transducer transmitting the pulse.

In the situation shown in FIG. 12, the reflection point considered is $P_{19,2}$ and even in this case the distances between the point $P_{19,2}$ and the transducers, shown by arrows, increase as we move away from the transducer $T_2$, such that the component of the reception signal of each transducer concerning the reflection signal of the point $P_{19,2}$ will be found by applying a time delay $\Delta t$ corresponding to such distances when reading such signal by means of said processing means 113.

Thus it is possible to find for each transducer the components of the reception signal which contain information that comes from the reflection signal of a predetermined reflection point in the body under examination coinciding with a predetermined point of the grid, by applying appropriate windows to the reception signal, shifted over time according to the appropriate delays.

With reference to FIGS. 11 and 12, the component of the reflected signal will have the maximum delay when reaching the transducer $T_n$, while in FIG. 13, where the reflection point considered is the point $P_{10,13}$, the reflection components of such point will have a smaller delay in the intermediate region of the transducer array 3 and higher delays at the ends of the transducer array 1.

Figure 14:
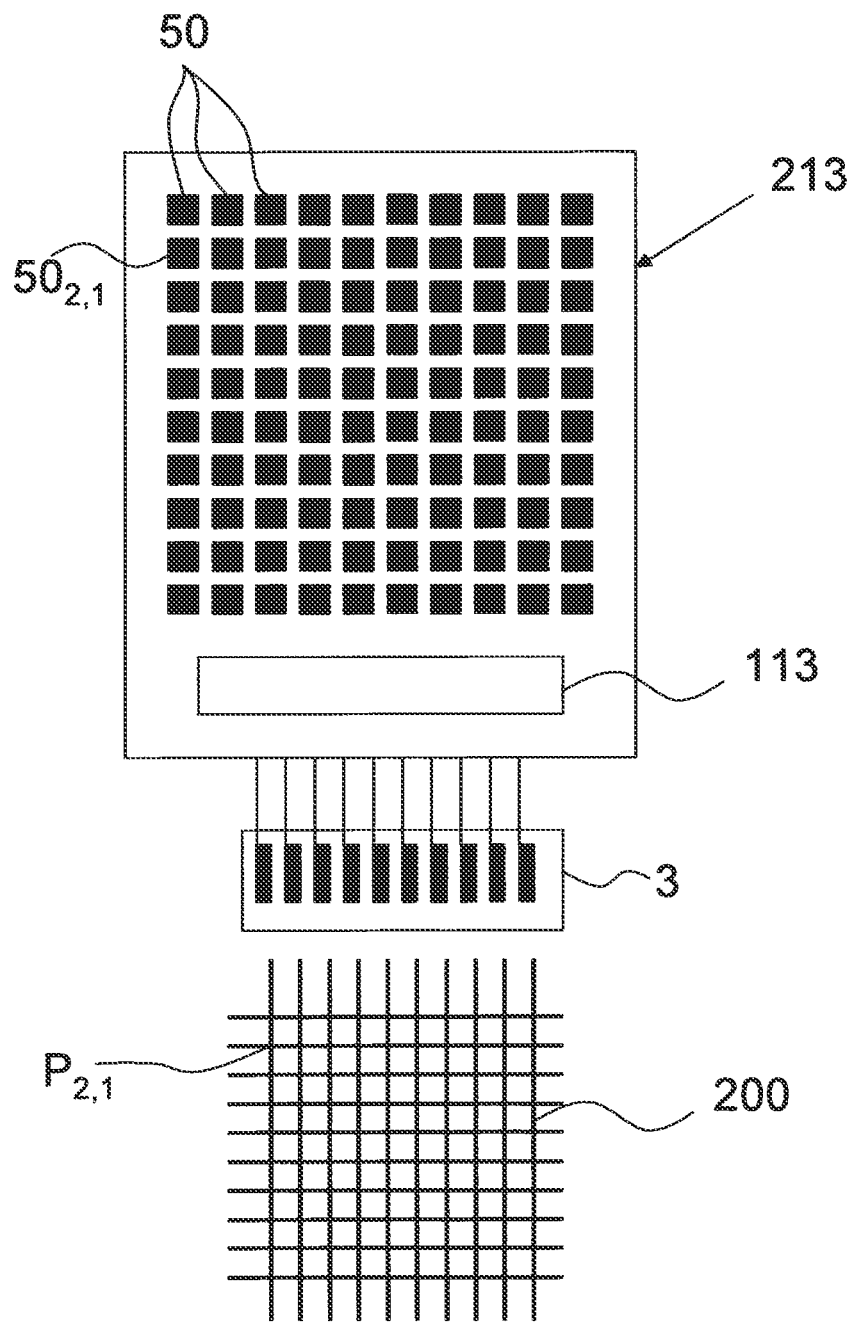
FIG. 14 is a schematic and simplified view of the storage of the signal components concerning the individual reflection points into individual storage cells.

FIG. 14 schematically shows the storage of the signal components concerning the individual reflection points in individual storage cells 50 provided in the storage area 213 described with reference to the previous figures.

That storage is made by said processing means 113, which receive the individual reception signals from the transducer array 1 and combine them by applying the time delays such that the components in each reception signal concerning each reflection signal and consequently each reflection point are summed together.

Such values are stored into the cells 50, thus obtaining a set of reflection signals that corresponds to the components of the reflected signal concerning each point on the grid 200.

This means that there is a one-to-one correspondence between the reflection features of a point of the body under examination corresponding to a point of the grid, for example $P_{2,1}$ and the value stored within the relevant storage cell, in this case $50_{2,1}$.

Figure 15:
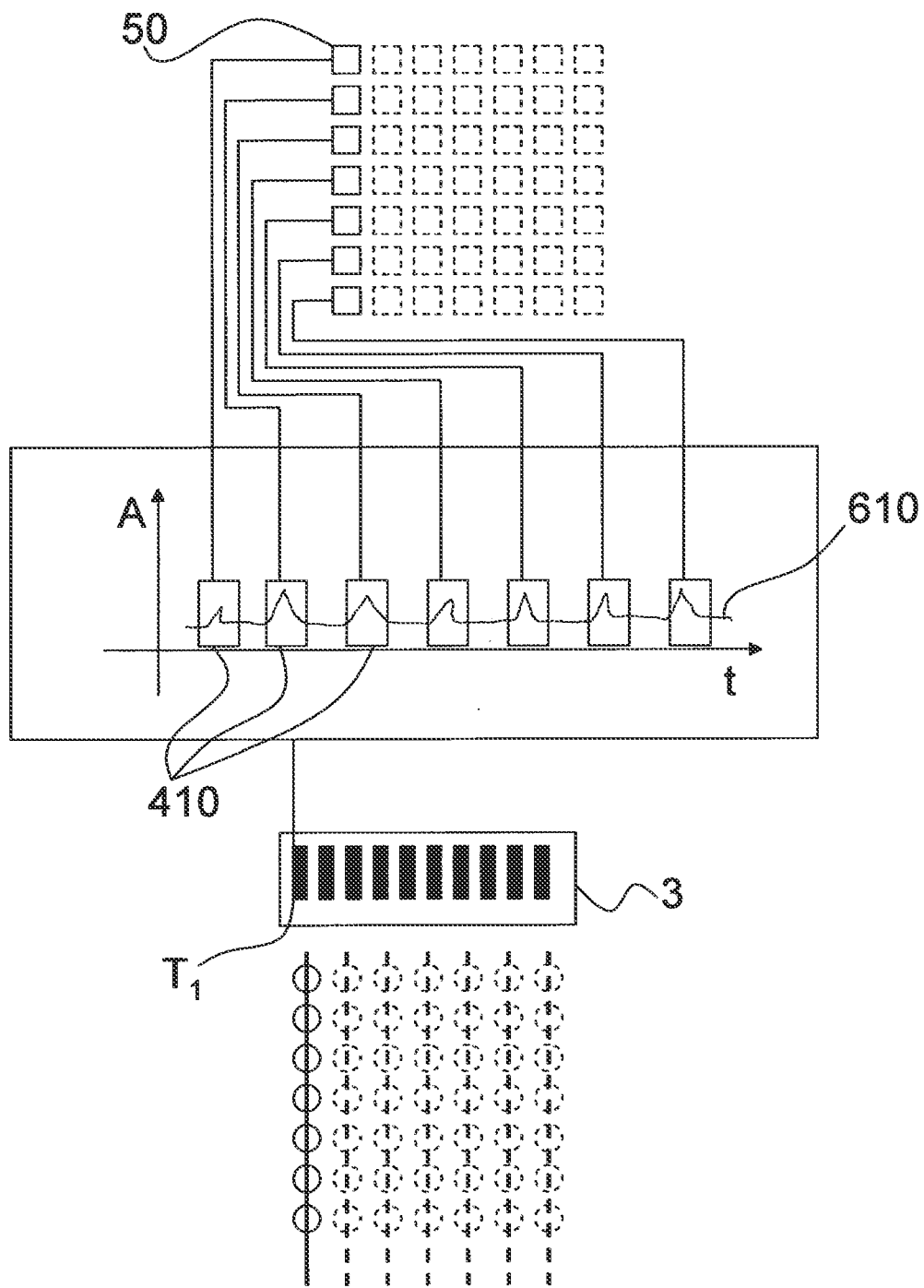
FIG. 15 is a schematic and simplified view of the determination in a reception signal of a transducer of the components concerning every individual reflection point on the grid and their storage into corresponding storage cells.

FIG. 15 schematically shows the determination into a reception signal of one transducer of the components relevant to each individual reflection point on the grid after a single transmission and their storage into corresponding storage cells.

In order to do that, the means 113 processing the reception signals combine together the reception signals provided by the individual transducers $T_1 \ldots T_n$.

Such combination occurs with the relative time shifts of the reception signals of the individual transducers $T_1 \ldots T_n$. The shifts are such that the individual components of the reception signals of the individual transducers $T_1 \ldots T_n$ are combined together. Those components correspond to the component of the reflected signal generated by the reflection of the transmission pulse by a predetermined reflector of the structure of the body under examination, which is in a predetermined position with respect to the array of transducers 1.

The time shift of the reception signals for defining the reflection signal of the transmission pulse by each of said predetermined reflection points is defined beforehand according to the predetermined relative distances between the individual reflection points.

Thus the determination of the reflection signal occurs by combining the components of the reception signals of the individual receiving transducers. Those components fall within time intervals of the reception signals having those delays and derive from the corresponding components of the reflection signal determined by each of the predetermined reflection points.

This can be clearly seen in FIG. 15, where, after a single transmission of an acoustic transmitting pulse in the form of a spherical wave by a single transducer, the transducer $T_1$ receives a reception signal 610 which is analyzed by the processing means 113.

The processing means 113 define, by means of time windows 410 arranged according to the predetermined delays corresponding to the predetermined distances of the points on the grid 200 from the transducer $T_1$, the components of the reception signal concerning the reflection signal of each point on the grid, which are stored within the corresponding storage cells 50.

Figure 16:
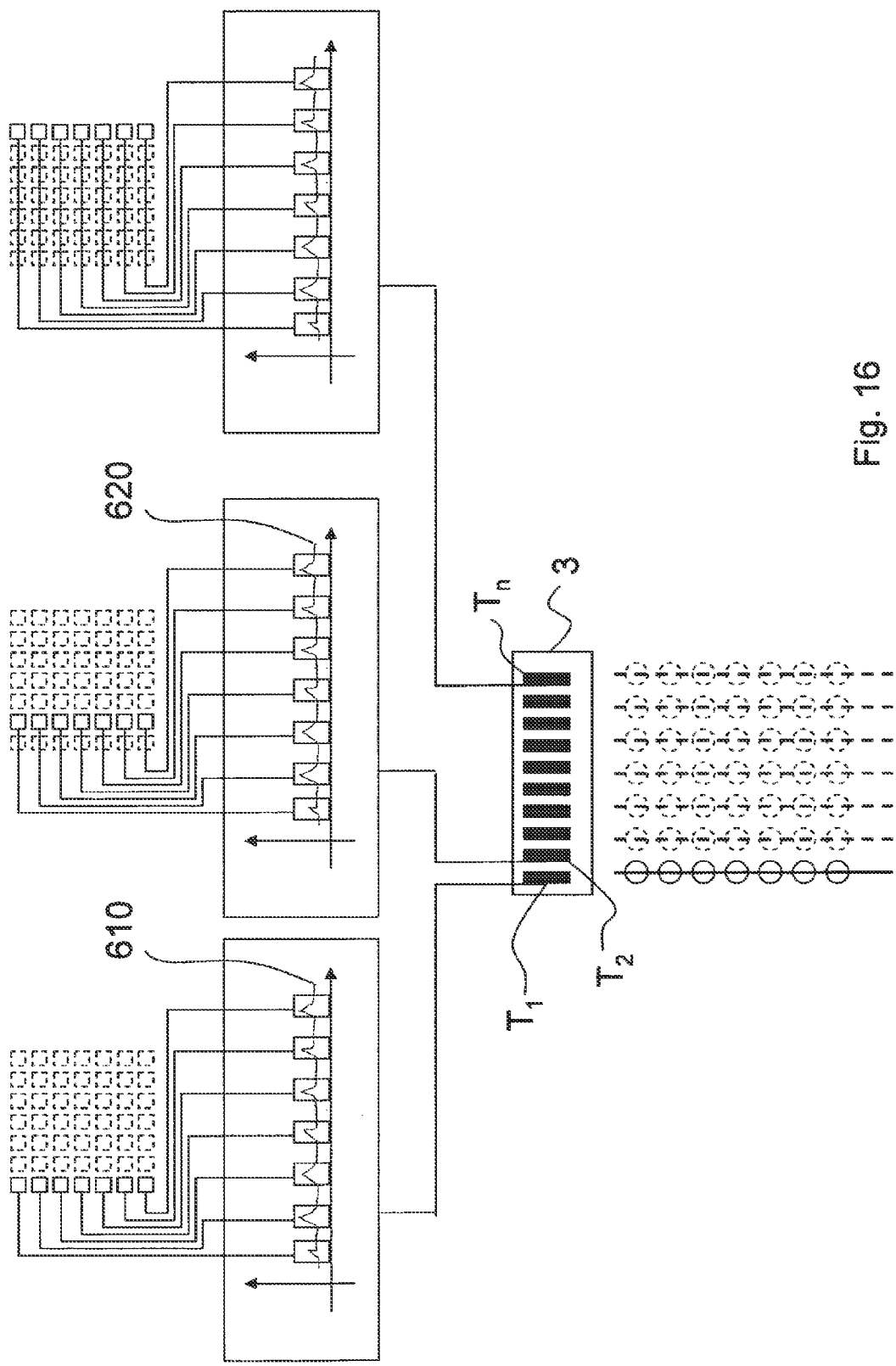
FIG. 16 is a schematic and simplified view of the storage in storage cells of the values corresponding to the reflection signals of each point on the grid.

The same procedure occurs for each transducer $T_1 \ldots T_n$, such as shown in FIG. 16, where, by decomposing each reception signal 610, 620 etc. of each transducer it is possible to define the set of reflection signals.

Such determination of the set of reflection signals by the individual reflection points of the grid of predetermined reflection points is therefore carried out for each spherical transmission pulse transmitted by a different transmitting point and the sets of reflection signals for each one of the spherical transmission pulse transmitted by the individual transmitting points are separately stored.

To this end, it is possible to provide additional arrays of storage cells 50, each one intended to store the different sets of reflection signals, each one concerning a single transmission.

In a one embodiment, the storage cells are virtual storage addresses on a single physical storage unit, and a program manages such storage unit.

Starting from the sets of the stored reflection signals, the processing means 113 generate the image along the scan plane or slice of the body under examination by summing the reflection signals of the sets of reflection signals generated by the individual spherical transmission pulses transmitted by the various transmitting points.

In one embodiment, the image is generated along the scan plane or slice of the body under examination by the mean of the reflection signals of the sets of reflection signals generated by the individual spherical transmission pulses transmitted by the various transmitting points.

In one embodiment, the sum or the mean of the reflection signals of the individual sets of reflection signals is separately calculated for each of the reflection points, that is, the sum or mean is calculated from the values of the reflection signal of each reflection point as stored in the various sets of reflection signals.

In that embodiment, the sum or mean of the reflection signals is calculated upstream of conversion into image data by the processing means 114.

In an alternative embodiment, the reflection signals of the individual sets of reflection signals are converted into image data and then separately stored. For each set of reflection signals, that sum or mean is calculated using the image data deriving from the individual sets of reflection signals.

FIG. 15 shows the determination of a sub-grid 210 smaller than the grid 200, whose peripheral points coincide with at least part of the points of said grid. Sub-grid 210 is formed of as many points as those contained in said grid 200, in the area delimited by the peripheral points of said sub-grid 210 or more.

Figure 17:
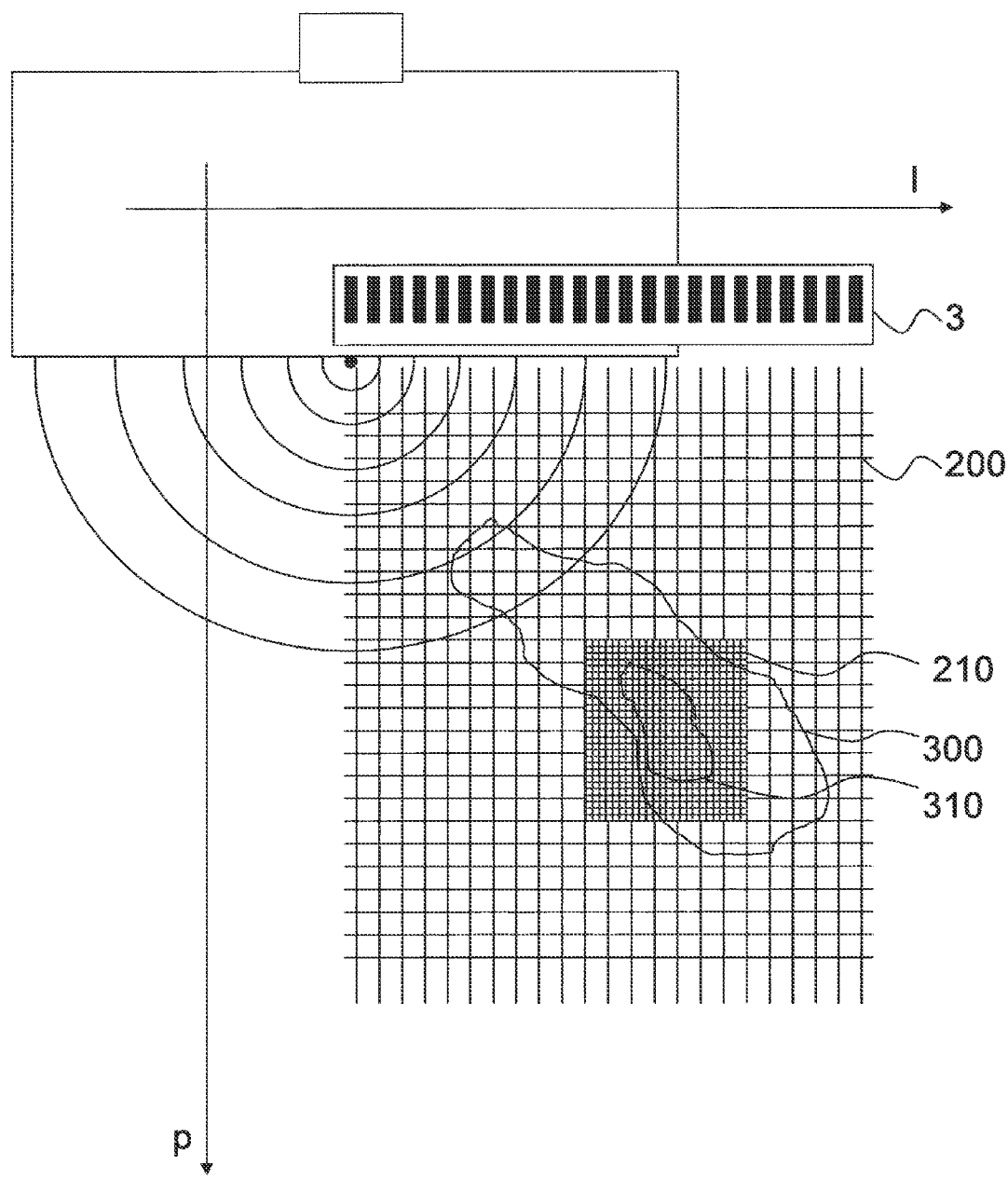
FIG. 17 shows the determination of a sub-grid for the detailed analysis of a limited area in the body under examination.

In the example of FIG. 17, therefore, a region of interest is defined corresponding to a particular structure of interest 310 into an obtained image, thus allowing the following acquisitions to be made in such region of interest.

The processing means 113 are intended for determining the sub-grid 210 and for the relative recalculation of the points constituting it.

In one embodiment, the number of points in the sub-grid 210 is the same as of the points of the grid 200, since it is defined by the number of transducers $T_1 \ldots T_n$ and by the computing power of the processing means 113.

In an alternative embodiment, the transducers used for scanning are provided in an amount smaller than the total amount and are limited to a reduced area surrounding or near the region of interest wherein said sub-grid 210 is defined.

In one embodiment, there is provided a user interface for displaying the image or video so obtained and for setting the perimeter of the sub-grid 210. A computational algorithm is provided for automatically defining the internal points of the sub-grid 210.

In another embodiment, the processing means 113 comprise means for forming and focusing an acoustic beam on the individual reflection points, referred to in the trade as receive/transmit beamformers.

Yet another embodiment, the array of transducers $T_1 \ldots T_n$ is a two-dimensional array generating scan volumes for the body under examination, in which acoustic pulses are transmitted and from which reflection pulses of the transmitted acoustic pulses are received.

In this case, the predetermined reflection points are arranged in a three-dimensional grid 200 within the scan volume, the transmitting points are arranged along the two-dimensional surface of the array of transmitting transducers, and each set of reflection signals comprises the reflection signals of the reflection points of the three-dimensional grid 200 of reflection points for forming a three-dimensional image.

The technique shown with reference to the two-dimensional embodiments can be easily extended also to three-dimensional image acquisition modes. In this case the probe is of the matrix array type and, therefore, the array of transducers is a two-dimensional array. The grid can be defined with a three-dimensional shape since all the above described concepts for a two-dimensional grid can be extended without inventive modifications to the three-dimensional grid and therefore to 3D ultrasound imaging.

The invention claimed is:

1. An apparatus for ultrasound image acquisition integrated into a casing of an ultrasound probe for ultrasound imaging apparatus, the probe comprising:
    an array of electro-acoustic transducers, each one of said electro-acoustic transducers transmitting ultrasound waves when powered with an electric excitation signal and generating an electric reception signal when impinged by an ultrasound wave or pulse generated by a reflection of ultrasound waves transmitted therefrom; and
    a communication line operatively coupling said array of electro-acoustic transducers to a generating unit through which each transducer of said array of transducers feeds reception signals to a processing unit, and through which electric excitation signals generated by said generating unit are fed to each transducer of said array of transducers for exciting said transducer to transmit ultrasound waves,
    wherein said generating unit is configured to generate and feed excitation signals to said array of transducers, and
    wherein at least said processing unit is fitted into the probe casing and comprises a converting unit converting reception signals into an image, and a unit generating video signals for generating an image on a display unit,
    further comprising a wireless communication unit configured to transmit between said probe and a remote unit displaying and storing said image as video signals,
    wherein the processing unit comprises a storage wherein sequences of time windows for exciting individual transducers to transmit ultrasound pulses are stored, said time windows being defined to cause an acoustic transmission pulse successively transmitted as a spherical wave from each of a plurality of transmitting points arranged along said array of electro-acoustic transducers,
    wherein sequences of time windows for reception of reflection pulses of the acoustic transmission pulse are stored, said reflection pulses of said acoustic transmission pulse being converted into a reception signal by each of the receiving transducers during a corresponding reception time window of each of said receiving transducers according to a position of said receiving transducers on said array, said reception time windows being calculated beforehand for each point of a set of predetermined reflection points arranged at a predetermined distance one from the other and forming a grid of said predetermined reflection points extending in a scan plane or slice along which a body under examination is imaged, such that, by successive transmission of said acoustic transmission pulse shaped as said spherical wave from each of a plurality of transmitting points arranged all along said array of electro-acoustic transducers, a set of reflection signals is defined from individual reflection points of said grid of said predetermined reflection points for each spherical transmission pulse transmitted by a different transmission point,
    wherein said converting unit calculates, in real time and every time, said time windows, and
    wherein said converting unit comprises an image forming storage, wherein said set of reflection signals for each of the spherical transmission pulses transmitted by individual transmitting points are stored by in a storage unit and the image along said scan plane or slice of the body under examination is generated by summing the reflection signals of sets of reflection signals generated by the individual spherical transmission pulses transmitted by various transmitting points.

2. The apparatus for ultrasound image acquisition according to claim 1, wherein said image forming storage comprises one or more storage cells where image data are stored for each set of reflection signals from the individual reflection points of said grid of said predetermined reflection points, such that said processing unit generates a single final image by summing the image data concerning each set of reflection signals contained in corresponding storage cells, each storage cell being univocally associated to an image pixel.

3. The apparatus for ultrasound image acquisition according to claim 2, wherein each storage cell is univocally associated to a reflection point of the grid of the reflection points and components of the reception signals corresponding to the reflection signals concerning said reflection point are stored therein, said components being determined by the reception time windows, each reception time window being calculated for receiving a reflection signal from a predetermined reflection point of the grid of the reflection points.

4. The apparatus for ultrasound image acquisition according to claim 1, wherein a function for determining a sub-grid smaller than said grid is provided, said sub-grid having peripheral points that coincide with at least part of the points of said grid, said sub-grid comprising as many points as the points contained in said grid at least in an area delimited by the peripheral points of said sub-grid.

5. The apparatus for ultrasound image acquisition according to claim 4, further comprising a user interface for displaying the image or video so obtained and for setting the perimeter of the sub-grid, a computational algorithm being provided for automatically defining internal points of said sub-grid.

6. The apparatus for ultrasound image acquisition according to claim 1, wherein each transducer of said array of transducers is connected to said processing unit and to said generating unit by a switch,
    said switch having two conditions, an operating condition that enables each transducer to receive/transmit electric excitation signals, and a non-operating condition that disables each transducer from receiving/transmitting electric excitation signals,
    a transition from said operating condition to said non-operating condition being set by the processing unit.

7. A method for ultrasound image acquisition comprising the steps of:
    transmitting ultrasonic transmission pulses into a body under examination;
    receiving reflection pulses from said body under examination;
    transforming said reflection pulses into reception signals;
    converting the reception signals into an image; and
    displaying said image,
    wherein the transmission pulses are transmitted from a plurality of electro-acoustic transmitting transducers and the reflection pulses being received by a plurality of electro-acoustic reflection transducers which are actuated respectively for transmission and reception according to predetermined rules focusing an acoustic beam transmitted or received on individual points or on two-dimensional or three-dimensional regions of the body under examination, wherein a predetermined fixed grid of reflection points in a scan plane or volume defined by an array of transmitting and receiving transducers is determined, and wherein time windows actuating the transducers for the reception or the transmission are defined only for the transmission or reception of signal contributions deriving from each of said reflection points of the predetermined grid, the signal contributions deriving from at least each reflection point of said grid of reflection points being stored separately for each different point, the signal contributions of a reflection signal of each reflection point being summed together and providing a signal corresponding to a pixel or voxel of an ultrasound image in a position corresponding to an image of the body under examination in said reflection point, a set of pixels and voxels so obtained being encoded as a video signal and transmitted by wireless mode to a remote reproducing/display unit, wherein the step of transmitting ultrasonic pulses towards a body under examination comprises:

causing the pulses to be generated by transmitting transducers which are grouped into the array of transmitting transducers, wherein the transmitting transducers are each connected to an electric excitation pulse generator and transform electric pulses into acoustic pulses, wherein the reception of the reflection pulses generated upon reflection of the transmission pulses by structural elements of the body under examination are caused to have acoustic reflector features receivable by receiving transducers, wherein the receiving transducers are grouped into the array of the receiving transducers and are each connected to a processing unit, and wherein each receiving transducer provides the processing unit with the reception signal generated by excitation of the receiving transducer upon reception of a reflection acoustic signal impinging upon the receiving transducer;

causing said processing unit to combine the reception signals provided by the individual receiving transducers, wherein said combining occurs with time shifts of the reception signals of the individual receiving transducers based on a relative position of said receiving transducer on said array, wherein said time shifts are such that individual components of the reception signals of the individual receiving transducers are combined together, said components corresponding to components of the reflection signal generated by the reflection of the transmission pulse by a predetermined reflector of a structure of the body under examination, said structure being in a predetermined position with respect to the array of the receiving transducers;

repeating said step of causing said processing unit to combine the reception signals of the individual receiving transducers with different time shifts, thereby obtaining a combination of the components of the reception signals caused by the reflection of a transmission signal by each of the reflectors of the structure of the body under examination in a predetermined scan plane or a predetermined slice of the body under examination, said scan plane or said slice being parallel to a direction of propagation of the transmission pulses and the reflection signals;

defining a set of predetermined reflection points arranged at a predetermined distance from each other and forming a grid of said predetermined reflection points, said grid extending in the scan plane or slice along which the body under examination is imaged;

defining the time shift of the reception signals for determining the transmission pulse reflection signal from each of said predetermined reflection points beforehand according to predetermined relative distances between the predetermined reflection points, wherein a determination of the reflection signal occurs by combining the components of the reception signals of the individual receiving transducers, said components falling within time intervals of the reception signals having delays, said components deriving from corresponding components of the reflection signal determined by each of said predetermined reflection points;

successively transmitting an acoustic transmission pulse in a form of a spherical wave from each of a plurality of transmitting points all along the array of transmitting transducers;

determining a set of reflection signals from individual reflection points of said grid of predetermined reflection points for each spherical transmission pulse transmitted by a different transmission point, and separately storing said sets of reflection signals for each of the spherical transmission pulses transmitted by the individual transmitting points; and generating the image along the scan plane or slice of the body under examination by summing the reflection signals of the sets of reflection signals generated by individual spherical transmission pulses transmitted by various transmitting points.

8. The method for ultrasound image acquisition according to claim 7, wherein the image is generated along the scan plane or slice of the body under examination with the reflection signals of the sets of reflection signals generated by the spherical transmission pulses transmitted by the various transmitting points.

9. The method for ultrasound image acquisition according to claim 7, wherein a sum or a mean of the reflection signals of the individual sets of reflection signals is calculated either separately for each of the reflection points, or from values of the reflection signal of each reflection point as stored in various sets of reflection signals.

10. The method for ultrasound image acquisition according to claim 9, wherein said sum or mean of the reflection signals is calculated upstream from the conversion into image data by said processing unit.

11. The method for ultrasound image acquisition according to claim 9, wherein the reflection signals of the individual sets of reflection signals are converted into image data and then separately stored, for each set of reflection signals, said sum or said mean being calculated using the image data derived from the individual sets of reflection signals.

12. The method for ultrasound image acquisition according to claim 7, further comprising the step of determining a sub-grid smaller than said grid, said sub-grid having peripheral points that coincide with at least part of the points of said grid.

13. The method for ultrasound image acquisition according to claim 12, wherein said sub-grid comprises as many points as the point contained in said grid, at least in an area delimited by the peripheral points of said sub-grid.

14. The method for ultrasound image acquisition according to claim 7, wherein the transmitting transducers also act as receiving transducers, said receiving transducers being alternately actuated for the transmission and the reception of acoustic signals.

15. The method for ultrasound image acquisition according to claim 7, wherein the processing unit is configured to form and focus an acoustic beam on the individual reflection points, thereby operating as a receive/transmit beamformer.

16. The method for ultrasound image acquisition according to claim 7,
wherein the array of transmitting and receiving transducers is a two-dimensional array, said two-dimensional array of transducers generating scan volumes of the body under examination, acoustic pulses being transmitted into and reflection pulses of the transmitted acoustic pulses being received from said scan volumes, the predetermined reflection points being arranged in a three-dimensional grid within a scan volume, the transmitting points being arranged along a two-dimensional surface of the array of transmitting transducers, and
wherein each set of reflection signals comprising the reflection signals of the reflection points of the three-dimensional grid of reflection points forming a three-dimensional image.

17. The method for ultrasound image acquisition according to claim 7, wherein the acoustic pulses are transmitted by one or more subsets of transducers of the array, each of said one or more subsets having a smaller number of transducers than a total number of transducers of the array.

18. The method for ultrasound image acquisition according to claim 17, wherein, in at least one subset of transducers, at least the first or the last transducer of a subset are not coincident with the first or the last transducer of the array, with reference to their arrangement in the array.

19. The method for ultrasound image acquisition according to claim 17, wherein the transducers of at least one subset are alternated with inoperative transducers or transducers of another subset, or are in direct adjacent relation thereto.

* * * * *